(12) United States Patent
Landy, III et al.

(10) Patent No.: US 11,872,382 B2
(45) Date of Patent: Jan. 16, 2024

(54) RAPID INFUSER WITH ADVANTAGEOUS FLOW PATH FOR BLOOD AND FLUID WARMING, AND ASSOCIATED COMPONENTS, SYSTEMS, AND METHODS

(71) Applicant: Belmont Instrument, LLC, Billerica, MA (US)

(72) Inventors: John Joseph Landy, III, Billerica, MA (US); George G. Brusard, Lowell, MA (US); Tristan Dion, Billerica, MA (US); Yeu Wen Tseng, Watertown, MA (US)

(73) Assignee: Belmont Instrument, LLC, Billerica, MA (US)

( * ) Notice: Subject to any disclaimer, the term of this patent is extended or adjusted under 35 U.S.C. 154(b) by 974 days.

(21) Appl. No.: 16/464,115

(22) PCT Filed: Nov. 29, 2017

(86) PCT No.: PCT/US2017/063612
§ 371 (c)(1),
(2) Date: May 24, 2019

(87) PCT Pub. No.: WO2018/102354
PCT Pub. Date: Jun. 7, 2018

(65) Prior Publication Data
US 2020/0001022 A1    Jan. 2, 2020

Related U.S. Application Data

(63) Continuation of application No. 15/364,532, filed on Nov. 30, 2016, now Pat. No. 10,507,292, and a
(Continued)

(51) Int. Cl.
*A61M 5/44*    (2006.01)
*A61M 5/36*    (2006.01)
(Continued)

(52) U.S. Cl.
CPC ............... *A61M 5/445* (2013.01); *A61F 7/00* (2013.01); *A61F 7/007* (2013.01); *A61F 7/0085* (2013.01);
(Continued)

(58) Field of Classification Search
CPC .. A61M 2205/3368; A61M 2205/3653; A61M 5/36; A61M 5/44; A61M 5/445
See application file for complete search history.

(56) References Cited

U.S. PATENT DOCUMENTS 1,208,925 A  * 12/1916  Phillipson et al. ..... B25B 13/18
                                                   81/356
1,656,518 A    1/1928  Hammers
(Continued)

FOREIGN PATENT DOCUMENTS

CN    201012173 Y    1/2008
DE    4241830 A1    6/1994
(Continued)

OTHER PUBLICATIONS

International Partial Search Report, PCT/US2017/063612 (Rapid Infuser With Advantageous Flow Path for Blood and Fluid Warming, and Associated Components, Systems, and Methods, filed Nov. 29, 2017), issued by ISA/EPO, 2 pages, dated Mar. 7, 2018.
(Continued)

*Primary Examiner* — Quynh-Nhu H. Vu
(74) *Attorney, Agent, or Firm* — Choate, Hall & Stewart LLP; William R. Haulbrook; Peter A. Flynn

(57) ABSTRACT

The present disclosure provides improved technologies relating to medical fluid heating systems and apparatus. In certain embodiments, the present disclosure relates to systems and apparatus for heating a fluid and, more particularly, for quickly and controllably heating a flow of blood or a blood product, for example, for infusion into a patient or for
(Continued)

hyperthermia treatment. In particular, in a first aspect, the present disclosure is directed to a system and apparatus featuring single flow path fluid heating ("single path flow"). Moreover, in a second aspect, the present disclosure is directed to a system, apparatus, and related method for efficiently utilizing the thermal energy of an infusate stored in a reservoir ("slack time heating"). Furthermore, in a third aspect, the present disclosure is directed to a fluid heating system and apparatus featuring a vacuum release valve designed to prevent the undesired orientation of deformed inflow tubing ("vacuum release valve").

20 Claims, 17 Drawing Sheets

Related U.S. Application Data continuation of application No. 15/364,515, filed on Nov. 30, 2016, now Pat. No. 10,137,257, and a continuation of application No. 15/364,499, filed on Nov. 30, 2016, now Pat. No. 10,485,936.

(51) Int. Cl.
  *A61F 7/00* (2006.01)
  *A61F 7/12* (2006.01)
(52) U.S. Cl.
  CPC .......... *A61F 7/12* (2013.01); *A61M 5/36* (2013.01); *A61M 5/44* (2013.01); *A61F 2007/0059* (2013.01); *A61F 2007/0072* (2013.01); *A61F 2007/126* (2013.01); *A61M 2205/3368* (2013.01); *A61M 2205/3653* (2013.01)

(56) References Cited

U.S. PATENT DOCUMENTS

| | | | |
|---|---|---|---|
| 2,494,716 A | 1/1950 | McMahon et al. | |
| 2,550,584 A | 4/1951 | Mittelmann | |
| 2,886,771 A | 5/1959 | Vincent | |
| 3,046,378 A | 7/1962 | Holz | |
| 3,207,372 A * | 9/1965 | Evans | A61M 5/1411 604/254 |
| 3,315,681 A | 4/1967 | Poppendiek | |
| 3,388,230 A | 6/1968 | Cunningham et al. | |
| 3,399,536 A | 9/1968 | Walz | |
| 3,443,060 A | 5/1969 | Smith | |
| 3,475,590 A | 10/1969 | Pins | |
| 3,482,575 A | 12/1969 | Claff et al. | |
| 3,485,245 A | 12/1969 | Lahr et al. | |
| 3,518,393 A | 6/1970 | Besseling et al. | |
| 3,590,215 A | 6/1971 | Anderson et al. | |
| 3,614,385 A | 10/1971 | Horstmann | |
| 3,640,283 A | 2/1972 | Bhatia et al. | |
| 3,641,302 A | 2/1972 | Sargeant | |
| 3,713,341 A * | 1/1973 | Madsen | A61M 1/3639 73/715 |
| 3,812,315 A | 5/1974 | Martin | |
| 3,816,687 A | 6/1974 | Heitner | |
| 3,834,372 A | 9/1974 | Turney | |
| 3,853,479 A | 12/1974 | Talonn et al. | |
| 3,896,733 A * | 7/1975 | Rosenberg | A61M 1/02 604/9 |
| 4,032,740 A | 6/1977 | Mittelmann | |
| 4,038,519 A | 7/1977 | Foucras | |
| 4,061,141 A | 12/1977 | Hyden et al. | |
| 4,089,176 A | 5/1978 | Ashe | |
| 4,108,146 A | 8/1978 | Golden | |
| 4,167,663 A | 9/1979 | Granzow, Jr. et al. | |
| 4,191,182 A | 3/1980 | Popovich et al. | |
| 4,249,481 A * | 2/1981 | Adams | A61M 1/06 119/14.47 |
| 4,293,762 A | 10/1981 | Ogawa | |
| 4,309,592 A | 1/1982 | Le Boeuf | |
| 4,314,143 A | 2/1982 | Bilstad et al. | |
| 4,321,918 A | 3/1982 | Clark, II | |
| 4,322,275 A | 3/1982 | Jain | |
| 4,332,247 A * | 6/1982 | Mittleman | A61M 5/36 604/82 |
| 4,341,936 A | 7/1982 | Virgin | |
| 4,356,383 A | 10/1982 | Dahlberg et al. | |
| 4,381,004 A | 4/1983 | Babb | |
| 4,384,578 A | 5/1983 | Winkler | |
| 4,464,563 A | 8/1984 | Jewett | |
| 4,479,798 A | 10/1984 | Parks | |
| 4,511,777 A | 4/1985 | Gerard | |
| 4,532,414 A | 7/1985 | Shah et al. | |
| 4,540,401 A | 9/1985 | Marten | |
| 4,560,849 A | 12/1985 | Migliori et al. | |
| 4,563,170 A | 1/1986 | Aigner | |
| 4,574,876 A | 3/1986 | Aid | |
| 4,576,143 A | 3/1986 | Clark, III | |
| 4,602,140 A | 7/1986 | Sobolewski | |
| 4,638,135 A | 1/1987 | Aoki | |
| 4,678,460 A | 7/1987 | Rosner | |
| 4,680,445 A | 7/1987 | Ogawa | |
| 4,692,138 A | 9/1987 | Troutner et al. | |
| 4,694,976 A | 9/1987 | Schuetz | |
| 4,707,587 A | 11/1987 | Greenblatt | |
| 4,731,072 A | 3/1988 | Aid | |
| 4,747,826 A * | 5/1988 | Sassano | A61M 5/44 604/113 |
| 4,753,640 A * | 6/1988 | Nichols | A61M 25/003 D24/129 |
| 4,759,749 A | 7/1988 | Verkaart | |
| 4,782,212 A | 11/1988 | Bakke | |
| 4,791,262 A * | 12/1988 | Ando | H05B 6/108 219/674 |
| 4,801,777 A | 1/1989 | Auerbach | |
| 4,844,074 A | 7/1989 | Kurucz | |
| 4,847,470 A | 7/1989 | Bakke | |
| 4,855,552 A | 8/1989 | Marceau et al. | |
| 4,874,359 A | 10/1989 | White et al. | |
| 4,878,537 A | 11/1989 | Verkaart | |
| 4,906,816 A | 3/1990 | van Leerdam | |
| 4,907,145 A | 3/1990 | Cassidy | |
| 4,908,014 A | 3/1990 | Kroyer | |
| 4,938,279 A | 7/1990 | Betker | |
| 4,962,761 A | 10/1990 | Golden | |
| 5,003,145 A | 3/1991 | Nolle et al. | |
| 5,006,114 A * | 4/1991 | Rogers | A61M 39/26 604/245 |
| 5,062,775 A | 11/1991 | Orth | |
| 5,108,372 A | 4/1992 | Swenson | |
| 5,125,069 A | 6/1992 | O'Boyle | |
| 5,188,604 A | 2/1993 | Orth | |
| 5,245,693 A | 9/1993 | Ford et al. | |
| 5,250,032 A | 10/1993 | Carter, Jr. et al. | |
| 5,254,094 A | 10/1993 | Starkey et al. | |
| 5,319,170 A * | 6/1994 | Cassidy | A61M 5/44 219/676 |
| 5,344,568 A | 9/1994 | Kitaevich et al. | |
| 5,350,901 A | 9/1994 | Iguchi et al. | |
| 5,354,277 A | 10/1994 | Guzman et al. | |
| 5,381,510 A | 1/1995 | Ford et al. | |
| 5,408,577 A | 4/1995 | Weber, Jr. et al. | |
| 5,420,962 A | 5/1995 | Bakke | |
| 5,453,576 A * | 9/1995 | Krivitski | A61M 1/3656 600/481 |
| 5,476,444 A | 12/1995 | Keeling et al. | |
| 5,571,153 A | 11/1996 | Wallsten | |
| 5,690,815 A | 11/1997 | Krasnoff et al. | |
| 5,702,358 A | 12/1997 | Witherspoon et al. | |
| 5,833,654 A * | 11/1998 | Powers | A61M 39/0208 604/93.01 |
| 5,846,224 A | 12/1998 | Sword et al. | |
| 5,902,362 A * | 5/1999 | Paoluccio | B01D 46/4236 55/467 |

(56) References Cited

U.S. PATENT DOCUMENTS

| | | | |
|---|---|---|---|
| 5,913,814 A | 6/1999 | Zantos | |
| 6,017,493 A * | 1/2000 | Cambron | A61M 1/3638 604/6.15 |
| 6,045,648 A | 4/2000 | Palmgren et al. | |
| 6,117,076 A | 9/2000 | Cassidy | |
| 6,175,688 B1 | 1/2001 | Cassidy et al. | |
| 6,236,809 B1 | 5/2001 | Cassidy et al. | |
| 6,261,276 B1 * | 7/2001 | Reitsma | A61M 1/67 604/319 |
| 6,480,257 B2 | 11/2002 | Cassidy et al. | |
| 6,579,496 B1 | 6/2003 | Fausset et al. | |
| 6,607,027 B2 * | 8/2003 | Bosch | F28F 1/126 165/163 |
| 6,699,232 B2 * | 3/2004 | Hart | A61M 5/44 604/533 |
| 6,813,964 B1 * | 11/2004 | Clark | G01F 1/363 73/861.52 |
| 6,827,898 B1 | 12/2004 | Fausset et al. | |
| 7,048,136 B2 * | 5/2006 | Havens | B65D 51/1644 222/509 |
| 7,381,195 B2 * | 6/2008 | Mori | A61M 1/16 604/4.01 |
| 7,819,835 B2 | 10/2010 | Landy et al. | |
| 7,842,002 B2 | 11/2010 | Mantle | |
| 8,100,881 B2 | 1/2012 | Haifa | |
| 8,387,963 B2 | 3/2013 | Moutafis | |
| 8,439,960 B2 | 5/2013 | Burnett et al. | |
| 8,480,648 B2 | 7/2013 | Burnett et al. | |
| 8,672,884 B2 | 3/2014 | Burnett et al. | |
| 8,803,044 B2 * | 8/2014 | Kienman | A61M 1/1635 219/628 |
| 8,900,652 B1 | 12/2014 | Caballero et al. | |
| 9,737,672 B2 | 8/2017 | Landy et al. | |
| 9,770,547 B2 * | 9/2017 | Li | A61M 1/342 |
| 10,137,257 B2 | 11/2018 | Landy, III et al. | |
| 10,309,818 B2 * | 6/2019 | Gagne | A61M 1/1682 |
| 10,485,936 B2 | 11/2019 | Landy, III et al. | |
| 2001/0039441 A1 | 11/2001 | Ash | |
| 2003/0139788 A1 | 7/2003 | Eggers et al. | |
| 2005/0222653 A1 | 10/2005 | Noda et al. | |
| 2006/0089586 A1 | 4/2006 | Kaus et al. | |
| 2007/0051409 A1 | 3/2007 | Landy et al. | |
| 2009/0012450 A1 | 1/2009 | Shah et al. | |
| 2009/0012655 A1 | 1/2009 | Kienman et al. | |
| 2009/0043256 A1 * | 2/2009 | Landy | A61M 1/166 604/113 |
| 2009/0192446 A1 | 7/2009 | Landy, III et al. | |
| 2011/0009745 A1 * | 1/2011 | Seifer | G01F 1/663 600/437 |
| 2011/0196302 A1 | 8/2011 | Gildersleeve et al. | |
| 2012/0302995 A1 | 11/2012 | Hochareon | |
| 2015/0053725 A1 * | 2/2015 | Hingorani | B65D 47/088 222/484 |
| 2015/0190274 A1 * | 7/2015 | Landy | A61M 1/369 607/105 |
| 2016/0101228 A1 | 4/2016 | Landy, III et al. | |
| 2018/0147368 A1 | 5/2018 | Landy, III et al. | |
| 2018/0147369 A1 | 5/2018 | Landy, III et al. | |
| 2018/0147370 A1 | 5/2018 | Landy, III et al. | |

FOREIGN PATENT DOCUMENTS

| | | | |
|---|---|---|---|
| DE | 10206760 A1 * | 8/2003 | G01N 29/032 |
| GB | 1208925 A | 10/1970 | |
| WO | WO-9217040 A1 | 10/1992 | |
| WO | WO-9640331 A1 | 12/1996 | |
| WO | WO-00/02608 A1 | 1/2000 | |
| WO | WO-2018/102354 A1 | 6/2018 | |

OTHER PUBLICATIONS

International Provisional Opinion Accompanying Partial Search Report, PCT/US2017/063612 (Rapid Infuser With Advantageous Flow Path for Blood and Fluid Warming, and Associated Components, Systems, and Methods, filed Nov. 29, 2017), issued by ISA/EPO, 4 pages, dated Mar. 7, 2018.

International Search Report, PCT/US2017/063612 (Rapid Infuser With Advantageous Flow Path for Blood and Fluid Warming, and Associated Components, Systems, and Methods, filed Nov. 29, 2017), issued by ISA/US, 6 pages, dated May 9, 2018.

Written Opinion, PCT/US2017/063612 (Rapid Infuser With Advantageous Flow Path for Blood and Fluid Warming, and Associated Components, Systems, and Methods, filed Nov. 29, 2017), issued by ISA/US, 9 pages, dated May 9, 2018.

* cited by examiner

SECTION B-B

DETAIL A

DETAIL A

RAPID INFUSER WITH ADVANTAGEOUS FLOW PATH FOR BLOOD AND FLUID WARMING, AND ASSOCIATED COMPONENTS, SYSTEMS, AND METHODS

CROSS-REFERENCE TO RELATED APPLICATIONS

This application is a national stage entry of International Patent Application No. PCT/US2017/063612, filed Nov. 29, 2017, which claims priority to and the benefit of, U.S. patent application Ser. Nos. 15/364,499, 15/364,515, and 15/364,532 filed Nov. 30, 2016, each of which is incorporated herein by reference in its entirety.

BACKGROUND

To treat hemorrhaging (e.g., escape of blood from a ruptured vessel), it is often necessary to quickly infuse a substantial volume of fluid, e.g. whole blood, plasma or blood substitute, so as to maintain an adequate blood volume and circulation. However, to preserve blood or blood products, such materials are typically refrigerated, and it is necessary to warm them before infusion so as to avoid shock to a patient's system. The fluid or infusate (e.g., blood or blood product) is typically warmed using a fluid warmer. While it is desired to heat the infusate quickly, the temperature of the infusate should not exceed 40° C. to 42° C., since at higher temperatures, protein denaturation and red cell damage can occur. It is also important that any electrical power or potentials utilized in the heating process be effectively isolated from a patient.

Many rapid fluid warmers utilize a relatively large water bath reservoir which is preheated to 39° C. to 40° C. Water is pumped rapidly through the heat exchanger through which an infusate (blood or other infusate) is perfused, the two fluids being separated by a thin, usually metallic, heat exchange surface. These devices are relatively large and cumbersome due to the need for a water bath and water pump, as well as the heat exchanger and associated conduits. Additionally, there may be a risk of contamination of infusate with heat exchanger water.

Some dual flow path fluid warmers (e.g., the Belmont® Rapid Infuser, the Belmont® Hyperthermia Pump) utilize inductive or electro-magnetic heating techniques, involving a circular heat exchanger tailored to the shape of the magnetic field. The electro-magnetic heater includes a primary inductor (coil), generating an alternating magnetic field. A high current density in the secondary inductors (e.g., multiple thin ribbon like conductors placed in parallel) converts electric energy into thermal energy, so that the secondary inductors provide heat to a fluid that is in direct contact with the secondary inductors.

Fluid warmers may be utilized to supply fluids or infusates (e.g., blood, blood products) at relatively high flow rates (e.g., greater than 500 ml/min, or greater than 750 ml/min) particularly during medical emergencies. Administration of cold blood and other fluids at high flow rates using an in line warming system requires the delivery of high quantities of power to the fluids (e.g., to heat the fluid). To infuse cold fluids at a rate in excess of these levels would require more energy than the typical AC outlet can supply. To overcome this issue, certain systems store thermal energy in a separate fluid (e.g., water or oil, not infusate) for transferring the stored heat from the fluid to the infusate during times of need. Drawbacks of this approach include the necessity to later transfer energy to the infusate before/during infusion with the limited heat transfer rate of the system (e.g., due to a limited surface area between water/oil and infusate) and the potential contamination of the infusate by the fluid bath. Thus, better systems and methods to store and transfer thermal energy at high flow rates that minimize energy utilization and heat times are required.

Fluid warmers often have a sensor connected to inflow tubing to detect if an infusate reservoir is empty. Typically, the sensor comprises a transmitter and a receiver (FIG. 14A-14C), and measures velocity of ultrasound waves from the transmitter to distinguish between fluid and air, since ultrasound waves travel faster through fluids than air. The inflow tubing is located between the transmitter and the receiver. When the fluid level in the infusate reservoir is low (or zero), the pressure in the infusate reservoir and the inflow tubing can be lower than the atmospheric pressure. Therefore, the non-rigid inflow tubing deforms to minimize the pressure difference. The fluid out sensor measures this deformation in inflow tubing to detect fluid availability in the tubing and therefore, the reservoir.

The direction of deformation affects detectability of fluid levels in the inflow tubing by the sensor. The pressure difference between the inside of the non-rigid inflow tubing and the outside atmospheric pressure may result in the tubing collapsing from a circular cross-section into an elliptical cross-section. For example, the major axis of the elliptical cross-section of the collapsed inflow tubing may be perpendicular to a line between the transmitter and the receiver, or may be parallel to a line between the transmitter and the receiver. In some instances, e.g., where the major axis of the elliptical cross-section of the collapsed inflow tubing is perpendicular to a line between the transmitter and the receiver of the fluid out sensor, the sensor can detect the deformation due to the presence of air in the ultrasound beam path 129. However, in some instances, e.g., where the major axis of the elliptical cross-section of the collapsed inflow tubing is parallel to a line between the transmitter and the receiver, the sensor cannot detect the deformation due to lack of air in the ultrasound beam path 129. Improvements to existing sensors or incorporation of additional components that prevent the undesired orientation of a deformed inflow tubing are necessary for efficient and accurate functioning of the fluid heating system.

Components of fluid heating systems (e.g., heat exchangers, sensors, thermal energy storage) as described in U.S. Pat. Nos. 5,319,170, 7,819,835, and 9,737,672, each of which is incorporated herein by reference in its entirety, can be utilized in hyperthermia pump systems, and rapid fluid infusers.

Hyperthermia refers to the increase in an individual's body temperature above his or her normal range. Research has shown that temperatures greater than 41° C. can damage cancer cells, usually without significant damage of normal tissues. While there are multiple methods of inducing hyperthermia by either direct skin contact or radiant heating, many physicians favor an extracorporeal heat exchange (blood) circuit to raise patient body temperatures. Temperature and time may be interrelated with respect to tumor necrosis and risk of toxicity to normal cells. The inefficiency of tumor cells to dissipate heat due to their disorganized and compact vascular structure subjects the tumor to hypoxia, anaerobic metabolism, and local acidosis, making the tumor more vulnerable to injury and causing the tumor cells to undergo apoptosis.

Fluid heating systems are used regularly for various other kinds of medical treatments, in addition to hyperthermia treatment (e.g., treatment of hemorrhaging, treatment of tumors, treatment of circulating tumor cells (CTCs)). Further improvements to existing heating system technologies that ensure higher efficiencies and lower heating times at a wide range of flow rates are needed.

SUMMARY

The present disclosure provides improved technologies relating to medical fluid heating systems and apparatus. In certain embodiments, the present disclosure relates to systems and apparatus for heating a fluid and, more particularly, for quickly and controllably heating a flow of blood or a blood product, which may be needed, for example, for infusion into a patient or for hyperthermia treatment. In particular, in a first aspect, the present disclosure is directed to a system and apparatus featuring single flow path fluid heating ("single path flow"). Moreover, in a second aspect, the present disclosure is directed to a system, apparatus, and related method for efficiently utilizing the thermal energy of an infusate stored in a reservoir ("slack time heating"). Furthermore, in a third aspect, the present disclosure is directed to a fluid heating system and apparatus featuring a vacuum release valve designed to prevent the undesired orientation of deformed inflow tubing ("vacuum release valve").

With respect to the "single flow path" technology, a new fluid flow design is described herein that improves on prior strategies for heating infusate (e.g., blood, hyperthermia fluid). In particular, the design addresses an occluding issue that may result in overheating of the fluid and other inefficiencies. In certain embodiments, the design offers an improvement on inductive or electro-magnetic heating systems with toroidal dual flow paths.

For example, at low flow rates, the pressure drop from dual flow paths to the outlet may be insufficient to support flow through both paths, causing flow to occur only on a single side of the dual flow path. The other side of the dual flow path, therefore, may encounter stagnant or slow flow. The stagnant or slow flow in a toroidal heat exchanger may become an issue if, for example, blood or blood products have either been improperly anticoagulated or have had the anticoagulant compromised (e.g., mixed with lactated Ringer's or other solutions containing calcium). If the improperly treated blood or blood products coagulate in one of the flow paths with stagnant or slow flow, that flow path may become clogged. When the system with the occluded heat exchanger starts to supply heated fluids at a sufficiently high rate through the non-clogged path (e.g., with an increased heat supply), the heat exchanger may overheat, leading to system damage.

Embodiments of the present disclosure include new designs that provide a single flow path while retaining the advantages of certain existing blood warmers with inductive or electro-magnetic heaters. The newly designed single flow path heat exchanger would not experience stagnant flow even under conditions of improperly treated fluids or compromised anticoagulants at low rates that, in previous designs, may have caused overheating of a local flow path. The single flow path is found to obviate problems that may occur with the dual flow path system due to improper usage (e.g., use of blood or blood products that have not been properly treated or anticoagulated). In certain embodiments, the system retains advantages of toroidal electromagnetic heat exchangers, such as the ability to provide a wide range of accurately controlled flow rates, for example, flow rates that span a range from 2.5 mL/min to 1000 mL/min, and any range in between.

With respect to the "slack time heating" technology, embodiments described herein address a problem that arises with infusate heating systems that store thermal energy in a separate fluid (e.g., water, not infusate) for heat transfer to an infusate. Such systems, as previously noted, typically utilize a relatively large preheated water bath reservoir to transfer heat from the water to the infusate. Drawbacks of this approach include a relatively low heat exchange efficiency due to the limited heat exchange surface area between the water and the infusate. Another drawback is the potential contamination of the infusate by the water bath. Thus, "slack time heating" systems and methods are presented herein for efficiently utilizing the thermal energy of an infusate stored in a reservoir. In certain embodiments, an infusate is heated by an induction heater e.g., an electromagnetic heater, and thermal energy of thusly heated infusate (e.g., not water or other non-infusate heat exchange fluid) is stored in a reservoir. When the heater is not being actively used to infuse a patient, infusate is sent through the induction heater, is warmed, and is sent to a reservoir. Then, when the infusate is sent to the patient, fluid from the reservoir again passes through the induction heater before being sent to the patient. The amount of thermal energy that needs to be transferred to the fluid (e.g., infusate) is smaller, if the temperature difference the heater needs to achieve to heat the fluid (e.g., infusate) is lower (e.g., if the temperature of fluid going into the heater from the reservoir is higher). Thus, during a medical procedure, when the infuser is not needed, fluid can pass through the heater, and then reside in the reservoir until needed, thereby storing thermal energy. Thus, the system can heat the infusate more rapidly when the infusion is needed. As the system does not use other fluids to heat the infusate, the system also does not suffer from a risk of contamination, unlike water-based heat exchangers.

With respect to the "vacuum release valve" technology, embodiments of the present disclosure are directed to a fluid heating system that includes a vacuum release valve to prevent the undesired orientation of the deformed inflow tubing that occurs when the fluid levels in the tubing and/or reservoir are low or zero. The vacuum release valve supplies air to the tubing to reduce pressure difference between the inflow tubing and the surroundings, preventing the deformation of the inflow tubing.

In one aspect, the invention is directed to a system for heating a fluid, which comprises (a) a fluid separator comprising an inlet nozzle and an outlet nozzle, (b) a conduit (e.g., toroid-shaped) connected to the fluid separator, the conduit defining a central opening, (c) a primary inductor at least partially within the central opening and (d) one or more secondary inductors within the conduit (e.g., each of the one or more secondary inductors is ring-shaped, flat). In certain embodiments, the inlet nozzle directs an inlet flow to the conduit through the fluid separator. In certain embodiments, the conduit provides a single fluid flow path. In certain embodiments, each of the one or more secondary inductors is substantially parallel and the one or more secondary inductors are separated by gaps (or spaces). In certain embodiments, the primary inductor generates magnetic flux passing through the central opening when the primary inductor is energized. In certain embodiments, the outlet nozzle receives an outlet flow from the conduit through the fluid separator.

In certain embodiments, the primary inductor comprises a coil (e.g., a winding). In certain embodiments, the primary inductor is a moving magnet.

In certain embodiments, the conduit comprises a plurality of spacers which provides the gaps between the one or more secondary inductors.

In certain embodiments, the fluid separator comprises a divider (e.g., flat sheet) separating the inlet flow and the outlet flow. In certain embodiments, the fluid separator comprises a housing and a portion of the housing is thermally conductive to allow simultaneous infrared temperature detection of both the inlet flow and the outlet flow.

In certain embodiments, the fluid separator, the conduit, and the one or more secondary inductors are included as part of a disposable set which is configured to co-act with the primary inductor.

In certain embodiments, the fluid flow path has a conformation such that fluid is not in contact with the primary inductor.

In certain embodiments, each of the gaps has a distance of 0.001" to 0.1".

In certain embodiments, the one or more secondary inductors transfers heat to fluid within the single flow path. In certain embodiments, each of the one or more secondary inductors comprises conductive material (e.g., stainless steel).

In certain embodiments, the conduit comprises an insulator (e.g., polymer, plastic).

In certain embodiments, the system comprises one or more temperature detectors positioned for simultaneous detection of a temperature of the inlet flow and the outlet flow.

In certain embodiments, the system comprises a bubble trap for removing air bubbles from fluid flowing through the system.

In another aspect, the present invention is directed to an apparatus for heating a fluid comprising (a) a fluid separator comprising an inlet nozzle and an outlet nozzle, (b) a conduit (e.g., toroid-shaped) connected to the fluid separator, which defines a central opening, (c) a primary inductor at least partially within the central opening; and (d) one or more secondary inductors within the conduit (e.g., wherein each of the one or more secondary inductors is ring-shaped, flat). In certain embodiments, the conduit defines a single fluid flow path. In certain embodiments, each of the one or more secondary inductors is substantially parallel, and the one or more secondary inductors are separated by gaps (or spaces).

In certain embodiments, the conduit comprises a plurality of spacers which provides the gaps between the one or more secondary inductors.

In certain embodiments, the fluid separator comprises a divider (e.g., flat sheet) separating the inlet flow and the outlet flow. In certain embodiments, the fluid separator comprises a housing, and a portion of the housing is transparent to infrared light to allow simultaneous infrared temperature detection of both the inlet flow and the outlet flow.

In certain embodiments, the fluid separator, the conduit, and the one or more secondary inductors are included as part of a disposable set which is configured to co-act with the primary inductor.

In certain embodiments, the fluid flow path has a conformation such that fluid is not in contact with the primary inductor.

In certain embodiments, each of the gaps has a distance of 0.001" to 0.1".

In certain embodiments, the conduit comprises an insulator (e.g., polymer, plastic).

In certain embodiments, each of the one or more secondary inductors comprises a conductive material (e.g., stainless steel).

In certain embodiments, the apparatus comprises one or more temperature sensors.

In certain embodiments, the apparatus comprises a bubble trap for removing air bubbles from fluid flowing through the apparatus.

In another aspect, the present invention is directed to a disposable unit of a system for heating a fluid, which comprises a fluid separator comprising an inlet nozzle and an outlet nozzle, a conduit (e.g., toroid-shaped) connected to the fluid separator, the conduit defining a central opening, and one or more secondary inductors within the conduit (e.g., wherein each of the one or more secondary inductors is ring-shaped, flat). In certain embodiments, the inlet nozzle directs an inlet flow to the conduit through the fluid separator. In certain embodiments, the conduit provides a single fluid flow path. In certain embodiments, each of the one or more secondary inductors is substantially parallel, the one or more secondary inductors being separated by gaps (or spaces). In certain embodiments, the outlet nozzle receives an outlet flow from the conduit through the fluid separator.

In another aspect, the present invention is directed to a flow separator comprising (a) a housing, (b) an inlet nozzle, (c) an outlet nozzle, and (d) a divider separating an inlet chamber from an outlet chamber. In certain embodiments, the housing has a notch for securing the divider, (e.g., a width of the notch and a thickness of the divider are substantially identical). In certain embodiments, the inlet nozzle and the outlet nozzle are substantially parallel to each other (e.g. to allow flow through the outlet nozzle in an opposite direction to flow through the inlet nozzle). In certain embodiments, the divider has a solid upper portion to satisfactorily separate the inlet chamber from the outlet chamber (e.g., when the divider is secured in position in the notch of the housing), and the divider has a lower portion comprising a plurality of elongations to accommodate one or more secondary inductors. In certain embodiments, a portion the housing is thermally conductive to allow simultaneous temperature detection of both a fluid flowing through the inlet chamber and a fluid flowing through the outlet chamber. In certain embodiments, the flow separator has a thickness and/or is made of a material to allow accurate temperature detection of a fluid flowing through the inlet chamber and the outlet chamber. In certain embodiments, the separator and axis of the inlet and the outlet are substantially in the same plane.

In another aspect, the present invention is directed to a system comprising a flow separator as described above and one or more temperature detectors positioned for simultaneous detection of the temperature of fluid in the inlet chamber and the temperature of fluid in the outlet chamber.

In another aspect, the present invention is directed to a system for heating a fluid, which comprises a spiral inductive tube (e.g., which may be contained in a housing) defining a central opening, and a primary inductor at least partially within the central opening. In certain embodiments, the primary inductor generates magnetic flux passing through the central opening when the primary inductor is energized. In certain embodiments, the spiral inductive tube is part of a disposable set configured to co-act with the primary inductor. In certain embodiments, the spiral inductive tube provides a single flow path, and transfers heat to fluid within the single flow path. In certain embodiments, the spiral inductive tube is not in contact with the primary inductor.

In another aspect, the present invention is directed to a system for heating a fluid, which comprises (a) a fluid separator comprising an inlet nozzle and an outlet nozzle, (b)

a conduit (e.g., toroid-shaped) connected to the fluid separator, the conduit defining a central opening, (c) a primary inductor at least partially within the central opening, and (d) one or more secondary inductors within the conduit. In certain embodiments, the inlet nozzle directs an inlet flow to the conduit through the fluid separator. In certain embodiments, the conduit provides a single fluid flow path. In certain embodiments, each of the one or more secondary inductors is substantially sphere. In certain embodiments, the primary inductor generates magnetic flux passing through the central opening when the primary inductor is energized. In certain embodiments, the outlet nozzle receives an outlet flow from the conduit through the fluid separator.

In another aspect, the present invention is directed to a system for heating an infusate, which comprises a reservoir for containing an infusate, a fluid heater, a diversion valve, a patient line; and a recirculation line. In certain embodiments, the fluid heater comprises an inlet to receive the infusate from the reservoir. In certain embodiments, the diversion valve operates to direct a heated infusate from the fluid heater into either the patient line or the recirculation line. In certain embodiments, the patient line directs the infusate to a patient. In certain embodiments, the recirculation line directs the heated infusate to the reservoir, so that the system increases a temperature of the infusate in the reservoir.

In certain embodiments, the fluid heater is an induction heater (e.g., electro-magnetic heater). In certain embodiments, the fluid heater has a single flow path. In certain embodiments, the fluid heater receives electric power via an AC wall outlet or a battery.

In certain embodiments, the system further comprises a valve wand. In certain embodiments, the valve wand controlling a ratio of a flow in the patient line to a flow in the recirculation line.

In certain embodiments, the system further comprises a bubble trap for removing air bubbles from fluid flowing through the system.

In certain embodiments, the system further comprises one or more temperature detectors positioned for simultaneous detection of one or more temperature of the infusate.

In another aspect, the present invention is directed to a method for heating an infusate, which comprises heating an inlet infusate (e.g., from the reservoir or IV bag or other source) via a fluid heater, directing an outlet infusate into either a patient line or a recirculation line, providing the outlet infusate to a patient though the patient line when infusate is directed therethrough, and directing the outlet infusate to a reservoir though the recirculation line when infusate is directed therethrough, thereby providing heat to an infusate contained in the reservoir. In certain embodiments, the outlet infusate flowing from the heater.

In certain embodiments, the fluid heater is an induction heater (e.g., electro-magnetic heater).

In certain embodiments, temperature of the outlet infusate is higher than temperature of the inlet infusate.

In certain embodiments, the method further comprises measuring temperature of an inlet infusate, the inlet infusate flowing to the fluid heater from a reservoir.

In certain embodiments, the method further comprises mixing the infusate from the recirculation line and the infusate stored in the reservoir.

In another aspect, the invention directed to a system for heating a fluid, which comprises a conduit (e.g., toroid-shaped) defining a central opening, a primary inductor at least partially within the central opening, one or more secondary inductors within the conduit (e.g., wherein each of the one or more secondary inductors is ring-shaped, flat), the conduit defining a central opening, an inflow tubing connected to the conduit, and a vacuum release valve. In certain embodiments, each of the one or more secondary inductors is substantially parallel. In certain embodiments, the secondary inductors are separated by gaps (or spaces). In certain embodiments, the primary inductor comprises a coil (or a winding). In certain embodiments, when the primary inductor is energized, the coil generates magnetic flux passing through the central opening. In certain embodiments, when pressure in the inflow tubing is lower than atmospheric pressure, the vacuum release valve allows flow of air into the inflow tubing, thereby rapidly allowing the detection of a fluid out condition.

In certain embodiments, the system further comprises a reservoir for containing an infusate. In certain embodiments, the vacuum release valve is connected to the reservoir. In certain embodiments, the vacuum release valve is connected to the top of the reservoir. In certain embodiments, the vacuum release valve is connected to the bottom of the reservoir. In certain embodiments, the reservoir further comprises a tubing attached to the top of the reservoir, and the vacuum release valve is connected to the reservoir through the tubing.

In certain embodiments, the vacuum release valve allows flow of air into the inflow tubing when pressure in the inflow tubing is 1, 2, 3, 4, 5, 6, 7, 8, 9, or 10 psi lower than atmospheric pressure.

In certain embodiments, the conduit provides a single fluid flow path. In certain embodiments, the single fluid flow path has a conformation such that fluid is not in contact with the primary inductor.

In certain embodiments, the system further comprises a fluid separator comprising an inlet nozzle and an outlet nozzle, wherein the inlet nozzle directs an inlet flow to the conduit through the fluid separator and the outlet nozzle receives an outlet flow from the conduit through the fluid separator.

In certain embodiments, the conduit comprises a plurality of spacers which provides the gaps between the secondary inductors.

In certain embodiments, wherein the one or more secondary inductors transfers heat to fluid within the conduit.

In certain embodiments, the system further comprises a bubble trap for removing air bubbles from fluid flowing through the system.

In another aspect, the invention directed to a disposable unit of a system for heating a fluid, which comprises a conduit (e.g., toroid-shaped) defining a central opening, one or more secondary inductors within the conduit (e.g., wherein each of the one or more secondary inductors is ring-shaped, flat), an inflow tubing connected to the conduit, and a vacuum release valve. In certain embodiments, each of the one or more secondary inductors is substantially parallel.

In certain embodiments, the disposable unit further comprises a reservoir for containing an infusate. In certain embodiments, the vacuum release valve is connected to the reservoir. In certain embodiments, the vacuum release valve is connected to the top of the reservoir. In certain embodiments, the vacuum release valve is connected to the bottom of the reservoir. In certain embodiments, the reservoir further comprises a tubing attached to the top of the reservoir, and the vacuum release valve is connected to the reservoir through the tubing.

In certain embodiments, the disposable unit comprises a fluid separator comprising an inlet nozzle and an outlet nozzle. In certain embodiments, the conduit defines a single fluid flow path. In certain embodiments, the disposable unit further comprises a bubble trap for removing air bubbles from fluid flowing through the system.

Elements of embodiments involving one aspect of the invention (e.g., methods) can be applied in embodiments involving other aspects of the invention, and vice versa.

A more complete understanding of the invention, as well as further features and advantages thereof, will be obtained by reference to the following detailed description read in conjunction with the accompanying drawings.

BRIEF DESCRIPTION OF THE DRAWINGS

The Drawings, which are comprised of at least the following figures, are for illustration purposes only, not for limitation.

The foregoing and other objects, aspects, features, and advantages of the present disclosure may become more apparent and better understood by referring to the following description taken in conduction with the accompanying drawings, in which.

DEFINITIONS

Figure 1:
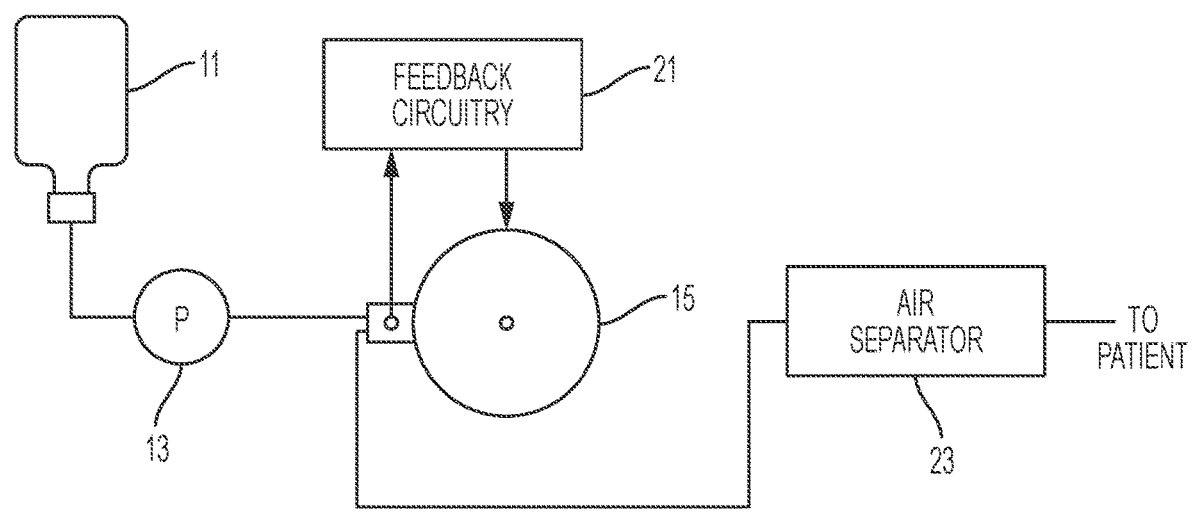
FIG. 1 is a schematic block diagram of a fluid heating apparatus, according to an illustrative embodiment of the present invention.

In order for the present disclosure to be more readily understood, certain terms are first defined below. Additional definitions for the following terms and other terms are set forth throughout the specification.

As used herein, the term "administration" typically refers to the administration of a composition to a subject or system. Those of ordinary skill in the art will be aware of a variety of routes that may, in appropriate circumstances, be utilized for administration to a subject, for example a human. For example, in certain embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In certain embodiments, administration may involve dosing that is intermittent (e.g., a plurality of doses separated in time) and/or periodic (e.g., individual doses separated by a common period of time) dosing. In certain embodiments, administration may involve continuous dosing (e.g., perfusion) for at least a selected period of time.

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

As used herein, the term "designed" refers to an agent (i) whose structure is or was selected by the hand of man; (ii) that is produced by a process requiring the hand of man; and/or (iii) that is distinct from natural substances and other known agents.

As used herein, the term "low flow rate" refers to a non-zero (e.g., no less than 1 ml/min) flow rate less than about 100 ml/min, or less than about 50 ml/min, or less than about 40 ml/min, or less than about 30 ml/min, or less than about 20 ml/min, or less than about 15 ml/min, or less than about 10 ml/min.

As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In certain embodiments, a patient is a human. In certain embodiments, a patient is suffering from or susceptible to one or more disorders or conditions. In certain embodiments, a patient displays one or more symptoms of a disorder or condition. In certain embodiments, a patient has been diagnosed with one or more disorders or conditions. In certain embodiments, the disorder or condition is or includes cancer, or presence of one or more tumors. In certain embodiments, the patient is receiving or has received certain therapy to diagnose and/or to treat a disease, disorder, or condition.

As used herein, the term "substantially" refers to the qualitative condition of exhibiting total or near-total extent or degree of a characteristic or property of interest.

As used herein, the term "treatment" (also "treat" or "treating") refers to any administration of a therapy that partially or completely alleviates, ameliorates, relives, inhibits, delays onset of, reduces severity of, and/or reduces incidence of one or more symptoms, features, and/or causes of a particular disease, disorder, and/or condition. In certain embodiments, such treatment may be of a subject who does not exhibit signs of the relevant disease, disorder, and/or condition and/or of a subject who exhibits only early signs of the disease, disorder, and/or condition. Alternatively or additionally, such treatment may be of a subject who exhibits one or more established signs of the relevant disease, disorder, and/or condition. In certain embodiments, treatment may be of a subject who has been diagnosed as suffering from the relevant disease, disorder, and/or condition. In certain embodiments, treatment may be of a subject known to have one or more susceptibility factors that are statistically correlated with increased risk of development of the relevant disease, disorder, and/or condition.

DETAILED DESCRIPTION

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The following description is for illustration and exemplification of the disclosure only, and is not intended to limit the invention to the specific embodiments described.

The mention herein of any publication, for example, in the Background section, is not an admission that the publication serves as prior art with respect to any of the claims presented herein. The Background section is presented for purposes of clarity and is not meant as a description of prior art with respect to any claim. All headers and subheaders are provided for the convenience of the reader—they are not intended to limit applicability of the content that follows them.

As mentioned above, the present disclosure relates to warming of fluid (e.g., blood, blood products, hyperthermia fluid, and more). The present disclosure encompasses system, apparatus, and/or methods of warming fluids.

Most rapid fluid warmers utilize a relatively large water bath reservoir which is preheated to 39° C. to 40° C. Water is pumped rapidly through a heat exchanger through which the infusate is perfused, the two fluids typically being separated by a thin, usually metallic, heat exchange surface. These devices are relatively large and cumbersome due to the need for the water bath and water pump, as well as a heat exchanger and associated conduits. Additionally, there may be a risk of contamination of infusate with heat exchanger water. Such devices accordingly are not ideal for use in emergency situations.

Other rapid fluid warmers utilize resistive heating (i.e., Joule heating) to increase temperature of the infusate. The resistive heaters are smaller than heaters with the water bath. However, resistive heaters are often inaccurate and can cause overheating the infusate. Typically, the infusate does not contact the resistive heater directly, receiving heat through a wall with a high thermal resistance (e.g., a wall of an infusate container made of plastic). The resistive heater maintains a high temperature difference between the heater and the infusate to compensate for the high thermal resistance of the wall or the infusate container. Therefore, a local temperature of the resistive heaters can reach up to about 80° C., denaturing proteins in the infusate.

Commercially available rapid fluid warmers are described in, for example, U.S. Pat. Nos. 5,319,170, 6,175,688, 6,236,809, 6,480,257, and 7,819,835, each of which is incorporated herein by reference in its entirety.

Some blood warmers (e.g., the Belmont® Rapid Infuser, the Belmont® Hyperthermia Pump) utilize inductive or electro-magnetic heating techniques, involving a circular heat exchanger tailored to the shape of the magnetic field. Fluid is introduced into the toroid at a point where the fluid path bifurcates with each half flowing on opposites sides of the toroid, until the two halves rejoin at the fluid output of the toroid. The electro-magnetic heater includes a primary inductor (coil), generating an alternating magnetic field. A high current density in the secondary inductors (e.g., multiple thin ribbon like conductors placed in parallel) converts electric energy into thermal energy, so that the secondary inductors provide heat to a fluid. The infusate is in direct contact with the secondary inductors and receives heat directly from the secondary inductors without involving a wall with a high thermal resistance. This effective heat exchange system of the Belmont® Rapid Infuser enables fluid (e.g., blood, blood products with temperature of 4 to 37.5° C.) to be heated to a target temperature (e.g., normothermia) in a single pass. The efficiency of the system is higher than other systems as heat is exchanged through direct contact between the infusate and secondary conductors without involving a wall (e.g., infusate container) with a high thermal resistance.

In these systems, a user can control heat flux to the fluid precisely, thus, the electro-magnetic heating system prevents overheating. The toroidal blood warmer is equipped with a large digital touch screen display (e.g., LCD type with water proof touch pad) that displays step-by-step instructions for easy use and control. The large touch screen continuously displays fluid temperature, total volume infused, line pressure, and both target and actual infusion rates. The blood warmer is also equipped with automatic air removal with two air detectors one at input and another at output. This ensures that no air bubbles are accidentally introduced into the patient. There are sensors and automatic alarms to avoid unsafe conditions, for example if the line becomes obstructed, when the reservoir is out of fluid or when other conditions occur. Other sensors include pressure transducer, temperature probes (e.g., infrared sensing), pump infusion rate sensor, open door detector, and valve activation sensors. The blood warmers may be powered by Alternating Current (AC) power or on battery (e.g., for mobility). Furthermore, the size of the Belmont® Rapid Infuser and the Belmont® Hyperthermia Pump is significantly smaller (e.g., IV-pole mountable) than other commercial fluid heaters and has an extra-long power cord (e.g., 15 foot) for increased mobility.

Embodiments described herein provide an improvement on the aforementioned toroidal heat exchangers with dual flow paths. For example, during operation of the system at low flow rates, the pressure drop from the flow paths to the outlet may be insufficient to support flow through both paths, causing flow to occur only on a single side of the dual flow path. The other side of the dual flow path, therefore, encounters stagnant or slow flow. Normally, this does not pose a concern; however, the stagnant or slow flow in a toroidal heat exchanger may create a potential issue when blood or blood products have either been improperly anticoagulated or have had the anticoagulant compromised (e.g., mixed with lactated Ringer's or other solution containing calcium). In such cases, clogs may occur. For example, if improperly treated blood or blood product coagulates in one of the flow paths which have stagnant or slow flow, that flow path may become clogged. When the system with the clogged flow path starts to supply heated fluids at a sufficiently high rate (e.g., with an increased heat supply to the heat exchangers), the clogged flow path can overheat due to insufficient supply of fluids.

Embodiments of the present disclosure include new designs that provide a single flow path. The newly designed single flow path heat exchanger would not experience stagnant flow even under conditions of low flow rates and improper or compromised anticoagulants that, in previous designs, may have resulted in overheating of a local flow path. The single flow path is found to obviate problems that may occur with the dual flow path system due to improper usage (e.g., use of blood or blood products that have not been properly anticoagulated).

Fluid Heating System

Figure 2:
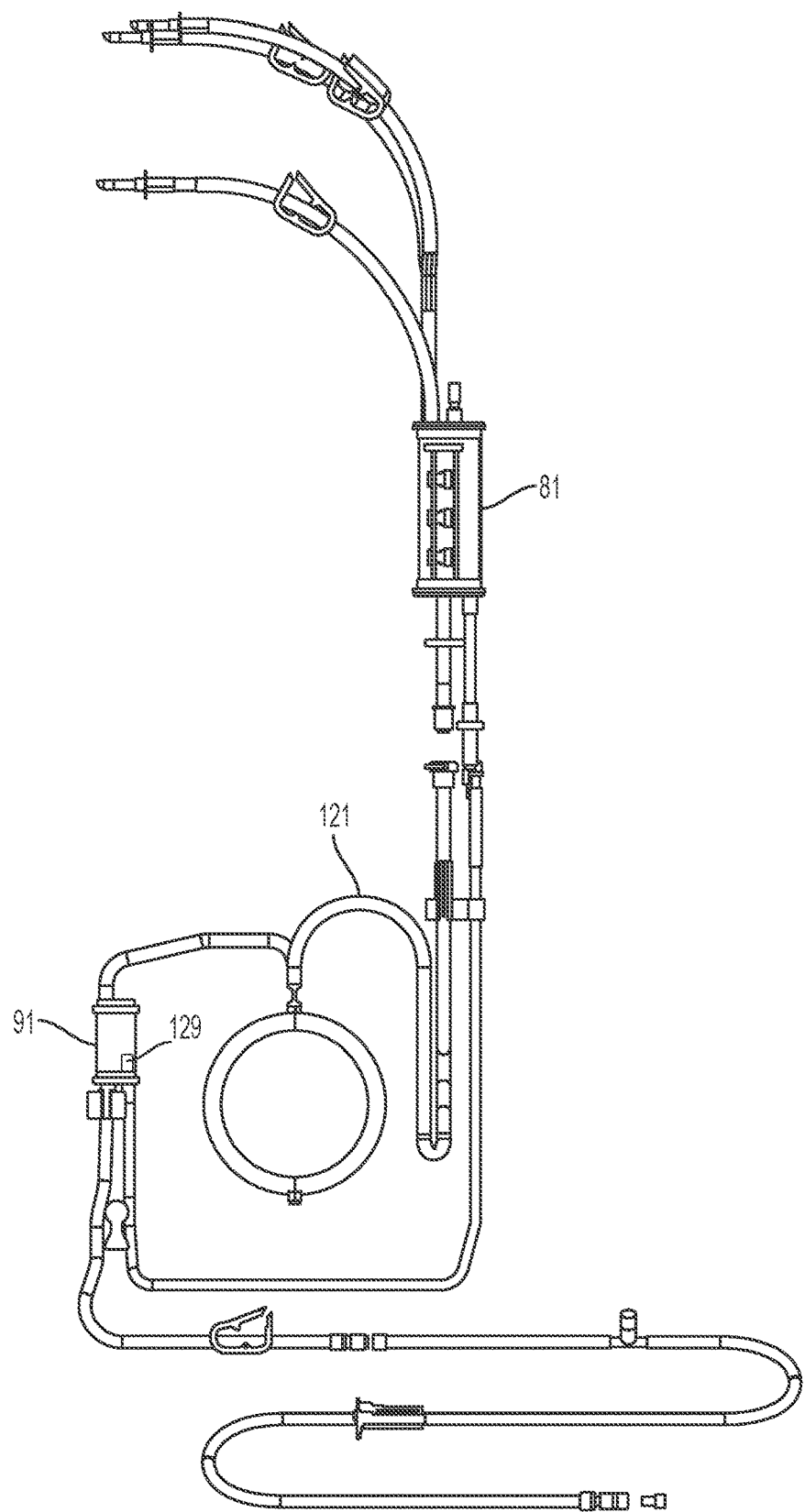
FIG. 2 is a front view of a disposable set, according to an embodiment of the instant invention.

In certain embodiments, as illustrated in FIGS. 1 and 2, a fluid heating system comprises a reservoir of infusate (e.g., blood, plasma or other solution). Fluid tubular lines and connectors of an infusion fluid disposable set, for example, as described in FIG. 2, direct fluid (e.g., infusate) to reservoirs of the infusion fluid disposable set. Additional tubular fluid lines and connectors of a disposable set direct fluid from reservoirs to and through a heater. Infusate drawn from reservoir 11 is driven by a pump 13 (e.g., roller pump) through an inductive heater constructed in accordance with the present disclosure. Heated fluid is directed into a patient tubular fluid feed line to a patient's body.

Figure 13:
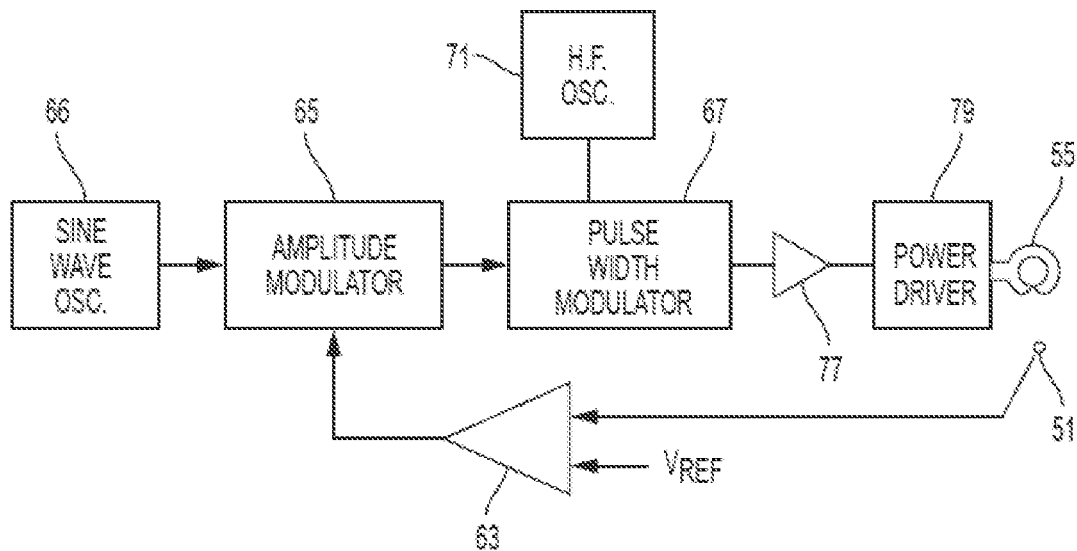
FIG. 13 is a schematic block diagram of circuitry for energizing the inductive heater of FIG. 3 and FIG. 4.

In heater 15, infusate is brought to a preselected temperature; control of the temperature is affected by feedback circuitry 21 that responds to outlet temperature, e.g., as sensed by a temperature sensor 51 of FIG. 13 to control the energization of an inductor, which effects the heat generation in the heater 15. This feedback circuitry is described in greater detail below. From the heater 15, the infusate passes through a separator 23, which removes any possible trapped air bubbles and then passes to the patient.

Figure 3:
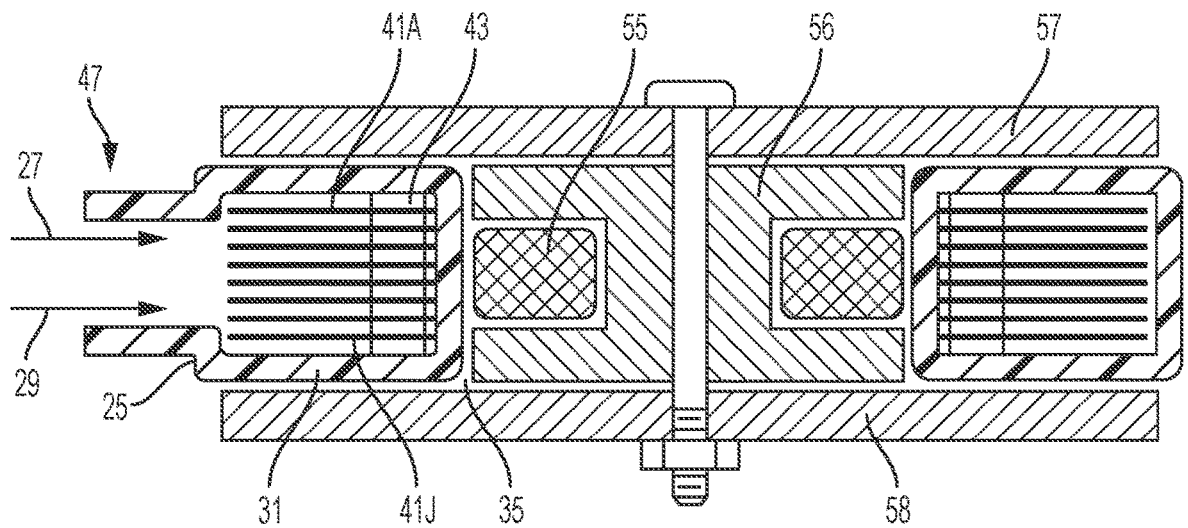
FIG. 3 is a cross-sectional view of an inductive heater employed, shown with a primary inductor, secondary inductors, a conduit, an inlet and an outlet, according to an illustrative embodiment of the present invention.
Figure 4:
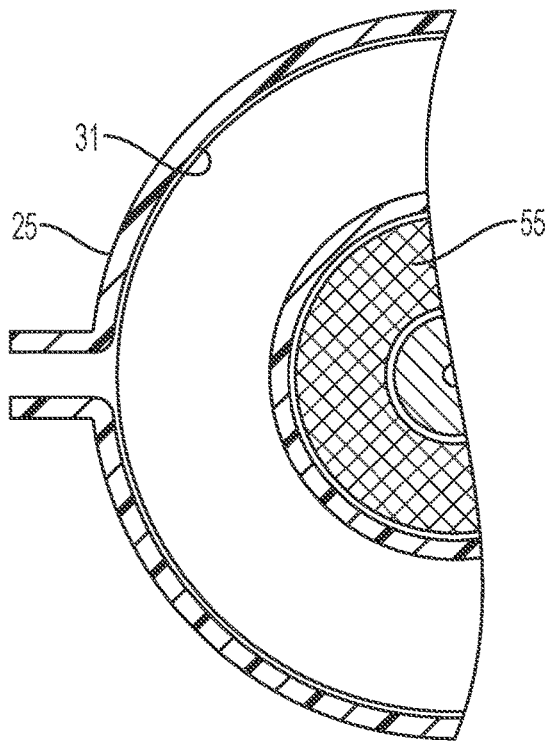
FIG. 4 is a plan view, with parts broken away, of the heater of FIG. 3.
Figure 5:
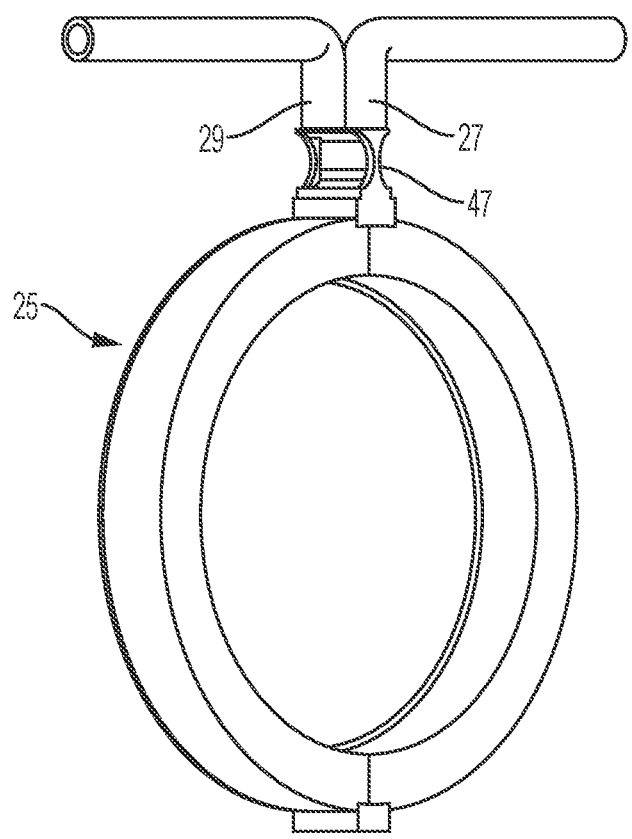
FIG. 5 illustrates a single flow path conduit with a fluid separator comprising an inlet nozzle and an outlet nozzle, according to an embodiment of the present invention.

In certain embodiments, as is illustrated in greater detail in FIGS. 3 and 4, the heater 15 involves a conduit or housing 25, which may be constructed of a suitable plastic material. A fluid separator 47 (e.g., made of the same plastic material) provides physical separation between an inlet 27 and an outlet 29, which are connected by a ring-like annular chamber 31. This defines a single circular flow path from the inlet 27 to the outlet 29 with an opening 35 in the middle. While the exemplary path is shown as forming a circle, it should be understood that other shapes could also be used, e.g. ovoid.

Within the chamber 31, there is a plurality of thin or ribbon-like secondary conductors 41A-41J. As illustrated, the conductors are in the shape of circular rings but it should be understood that other shapes could also be used, for example, ovoid.

A primary inductor comprising a winding 55 wound on a ferrite bobbin core 56 generates magnetic flux passing through the central opening and is inductively coupled to the plurality of secondary inductors 41A-41J for inducing local currents therein. The winding, however, does not surround the flow path. To improve the degree of coupling between the winding 55 and the secondary inductors 41A-41J, ferrite magnetic end plates 57 and 58 may be employed to extend the flux coverage.

Heat Exchanger

In certain embodiments, the heat exchanger comprises thin or ribbon-like secondary inductors 41A-41J contained in a chamber 31. As illustrated, the secondary inductors have a circular ring-like shape. In alternative embodiments, other shapes (e.g., beads, ovoid) can be used. In certain embodiments, the secondary inductors extend generally parallel to each other in a spaced relationship (spaced apart) with each secondary inductor passing through the flow path so as to heat the fluid. As will be apparent, fluid flowing from the inlet 27 to outlet 29 will pass through the spaces between the secondary inductors 41A-41J and will be in intimate thermal contact therewith.

In certain embodiments, the chamber 31 is circular and the secondary inductors 41A-41J are correspondingly formed as flat rings. This shape simplifies obtaining symmetry and uniform heating, but is not necessary to the mode of inductive heating. In other embodiments, other shapes are used. Spacing between adjacent secondary inductors 41A-41J is maintained by spacers 43.

In certain embodiments, where amounts and/or properties of the fluids in the heating system change, it is desirable to modify certain key parameters of the heat exchanger. When a fluid is in contact with a solid surface, heat flux between the fluid and the solid surface, which is the rate of heat energy transfers through the given surface per unit time, can be expressed as follows:

$$q = h \cdot \Delta T$$

wherein q is heat flux (W/m$^2$), h is a heat transfer coefficient (W/m$^2$·K), and ΔT is the difference in temperature between the solid surface and surrounding fluid area (K). The heat transfer coefficient is a function of the key parameters, for example, conductivity of the solid (e.g., the secondary inductors), gaps between the secondary inductors, etc. Total heat transfer from the solid surface (e.g., secondary conductors) to the fluid can be calculated by multiplying total surface area of the secondary conductors with the heat flux. Therefore, when one changes the fluid to be heated and/or operating conditions, it may be desirable to increase or decrease gaps between the secondary inductors, increase or decrease the number of secondary conductors, change the total surface area of secondary inductors, and/or change materials used in the construction of the secondary inductors. For example, in order to accommodate a higher heating capacity (e.g., higher flow rate), the number and/or the total surface area of the secondary conductors may be increased.

In certain embodiments, the secondary inductors are constructed, for example, of stainless steel. Other conductive materials such as conductive plastics might also be used. In certain embodiments, one or more conductive materials are selected from the group consisting of stainless steel, carbon (graphene), silver, copper, gold, aluminum, tungsten, zinc, nickel, lithium, iron, platinum, tin, carbon steel, lead, titanium, grain oriented electrical steel, manganin, constantan, mercury, nichrome, carbon (graphite) and combinations thereof. In certain embodiments, one chooses less conductive material (e.g., high resistance) to generate increased dissipation heat in the secondary inductors.

In certain embodiments, a conduit/chamber of the present disclosure has at least 1, 2, 4, 6, 8, 10, 12, 14, 16, 18, or 20 secondary inductors.

In certain embodiments, each gap between secondary inductors has a distance of about 0.001" to about 0.1", about 0.001" to about 0.1", about 0.001" to about 0.1", or about 0.02" to about 0.03".

In certain embodiments, total surface area of secondary inductors is about 1 to about 1000 in$^2$, about 1 to about 500 in$^2$, about 1 to about 250 in$^2$, about 10 to about 1000 in$^2$, about 10 to about 500 in$^2$, or about 10 to about 250 in$^2$.

Fluid Separator

In certain embodiments, a fluid separator is incorporated into a single flow path heating system. The fluid separator may enable a single flow path with minimal modification of the existing system (e.g., same primary inductor, tubing, etc.). An exemplary fluid separator is depicted in FIGS. 6A-6G, 7A, 7B and 8. The fluid separator comprises an inlet nozzle and an outlet nozzle. The inlet nozzle 27 directs unheated (e.g., cold) fluid to the single flow path, while the outlet nozzle 29 receives heated fluid from the single flow path. The inlet and outlet nozzle are substantially parallel to each other to allow flow through the outlet nozzle in an opposite direction to flow through the inlet nozzle.

In certain embodiments, the fluid separator has a housing. The housing contains two sections or chambers, an inlet chamber and an outlet chamber that are separated by a divider. The divider is discussed in more detail below. The inlet fluid (e.g., unheated infusate) first enters through the inlet 27 into the inlet chamber, and then moves into the single fluid path. The fluid while in the single fluid path is heated by the heat exchanger system described previously. The outlet fluid (e.g., heated infusate) exits from the single fluid path, then passes through the outlet chamber and the outlet 29.

Figure 6A:
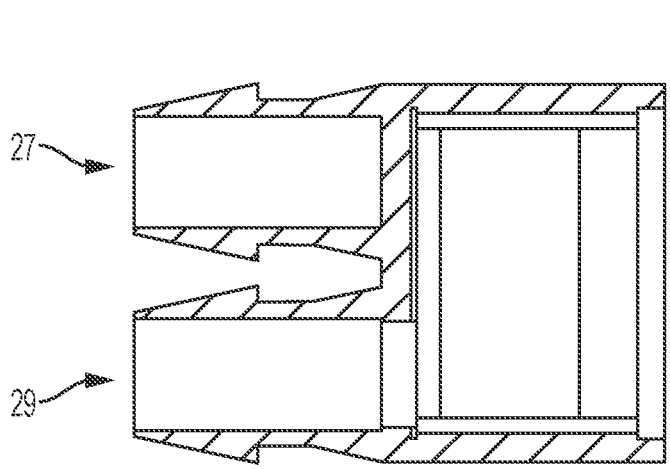
FIGS. 6A-6G illustrate a fluid separator, according to an embodiment of the present invention.
Figure 6B:
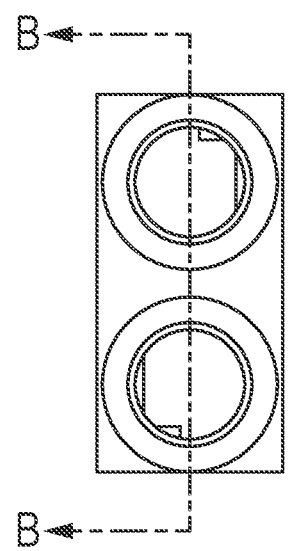
Figure 6C:
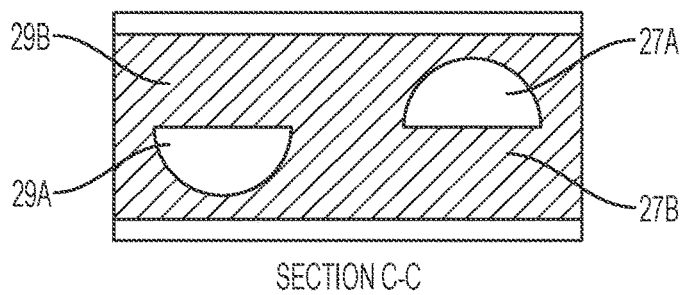
Figure 6D:
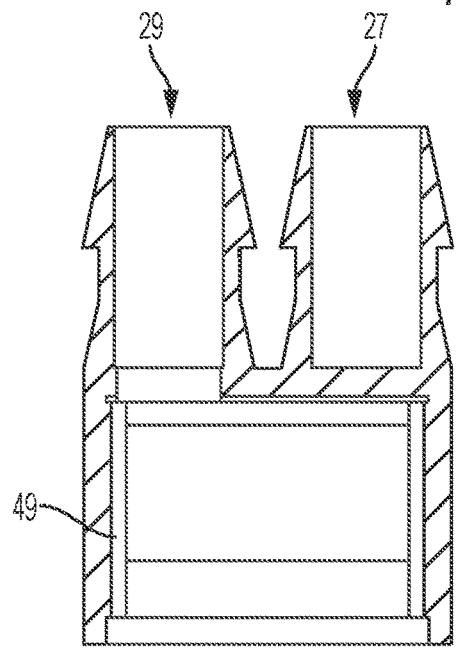

In certain embodiments, the inlet 27A and the outlet nozzles 29A are of semi-circular cross-section and are mirror images of each other along the length of the fluid separator (FIG. 6C). This design allows for the physical separation of the inlet fluid and the outlet fluid, and their flow to separate chambers.

Figure 6E:
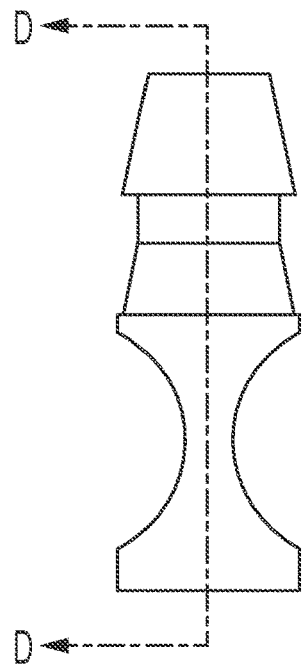
Figure 6F:
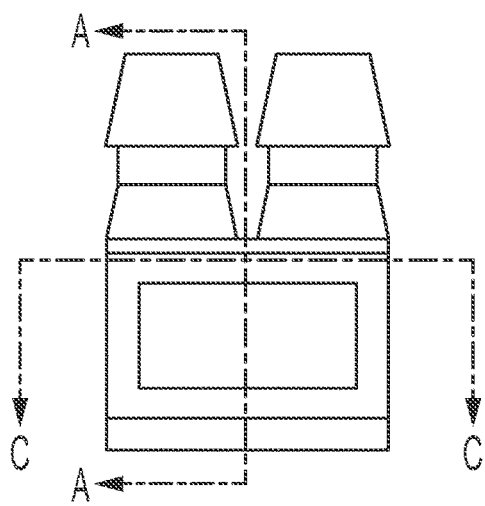
Figure 6G:
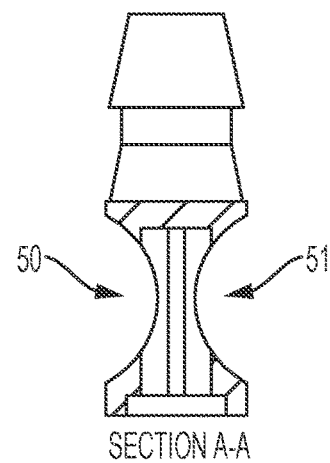
Figure 7A:
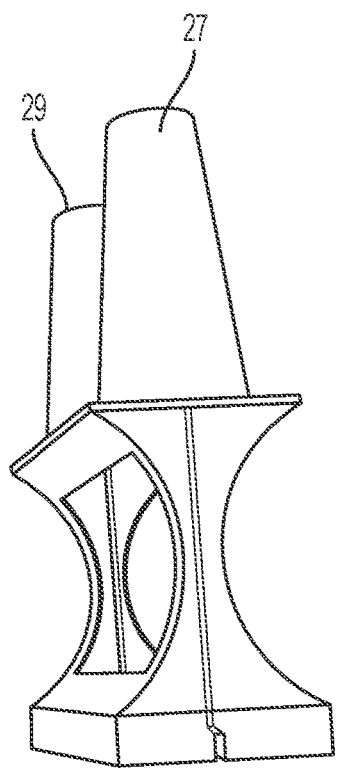
FIGS. 7A and 7B are optical images of a fluid separator, according to an embodiment of the present invention.
Figure 7B:
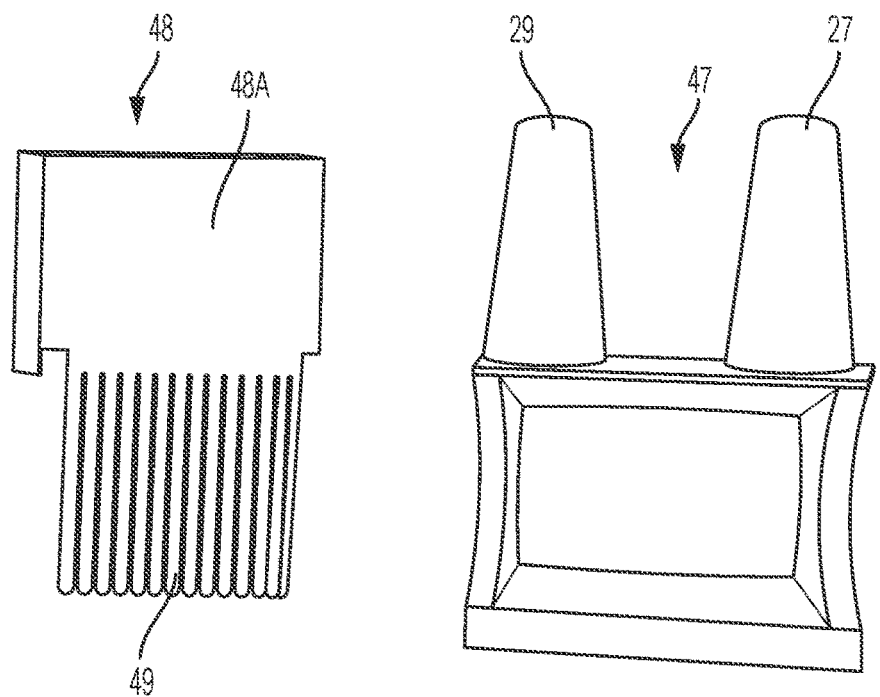

Temperatures of the inlet fluid and outlet fluid can be measured at exterior walls of the inlet chamber and the outlet chamber using temperature probes, respectively. A portion of the housing is sufficiently thermally-conductive, so that the temperature of the fluid (e.g., inlet unheated fluid, outlet heated fluid) is substantially identical to the temperature of the housing (e.g., outside of the inlet chamber, outside of the outlet chamber) that is in direct contact with the fluid. In certain embodiments, the housing comprises a notch that can secure a divider. In certain embodiments, the housing has two convex walls (50 and 51) at the inlet chambers and the outlet chambers, from the perspective of each of the inlet chamber and the outlet chamber as shown in FIGS. 6E and 6G. Temperature probes may measure inlet and outlet temperatures at these convex walls.

In certain embodiments, a fluid separator comprises a divider 48. The divider 48 separates the fluid separator housing into two sections or chambers—the inlet chamber and the outlet chamber, separating the unheated fluid in the inlet chamber and the heated fluid in the outlet chamber. The inlet nozzle 27 and the outlet nozzle 29 are connected to different sections or chambers of the fluid separator, so that the divider effectively separates the unheated fluid and the heated fluid.

The divider 48 may have a solid upper portion 48A to satisfactorily separate the inlet chamber from the outlet chamber when the divider is secured in the fluid separator. The divider may also have a lower portion comprising a plurality of elongations 49 to accommodate a plurality of secondary inductors. For example, each elongation of the divider 49 may occupy completely and block each gap between any two successive ring shaped secondary inductors in the plurality of secondary inductors 41A-41J, so that the elongations of the divider prevent mixing of the unheated fluid and the heated fluid that flow between the secondary inductors. In certain embodiments, each thickness of the elongations 49 is substantially identical to each gap between the secondary inductors. In certain embodiments, the width of the notch in the housing of the fluid separator and the thickness of the divider are substantially identical, so that the notch can secure the divider in the fluid separator.

In certain embodiments, the cross section of the inlet nozzle 27A, where it is connected to the inlet chamber is semi-circular as shown in FIG. 6C. Similarly, the cross section of the outlet nozzle 29A, where it is connected to the outlet chamber may be semi-circular. The semi-circular cross-sections of the inlet and the outlet are located on opposite sides of the fluid divider, so that the divider can separate the inlet and the outlet when the divider is positioned therebetween.

Figure 8:
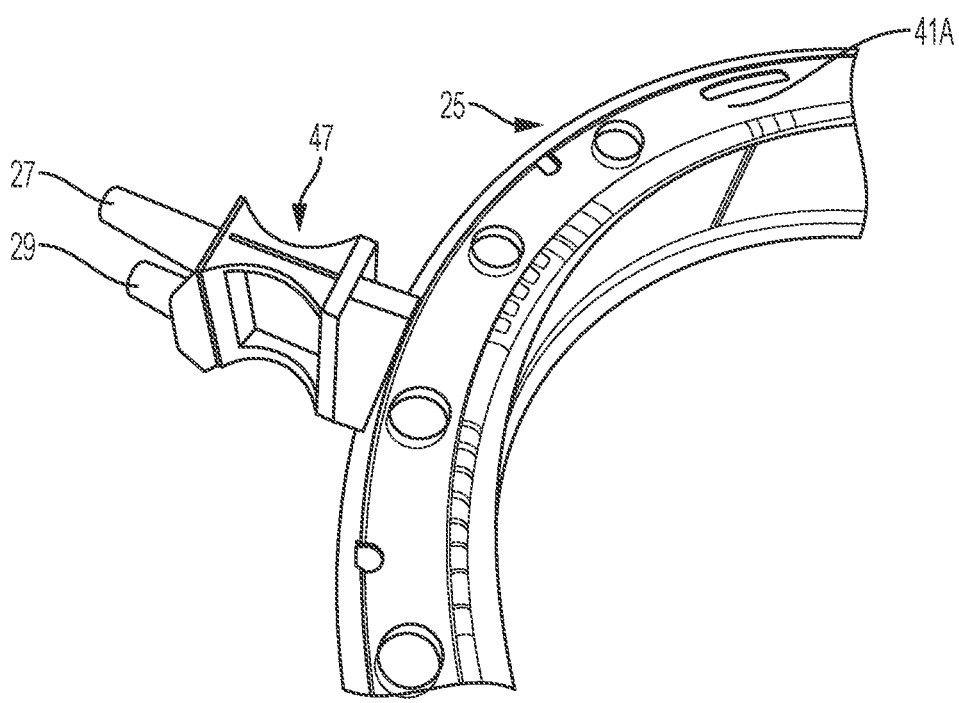
FIG. 8 shows a part of a disposable set with a fluid separator, a conduit and a plurality of secondary inductors, according to an embodiment of the present invention.
Figure 9A:
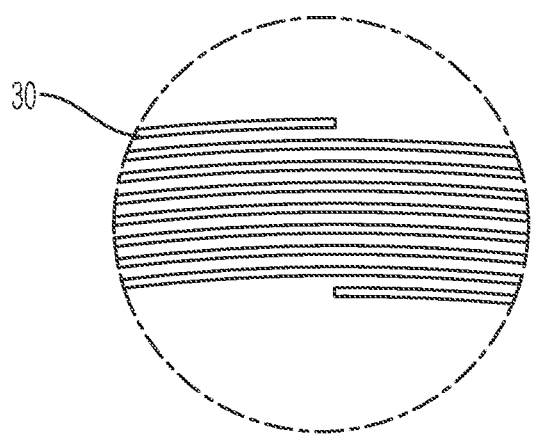
FIGS. 9A-9E depict a spiral inductive tube, according to an embodiment of the present invention.
Figure 9B:
Figure 9C:
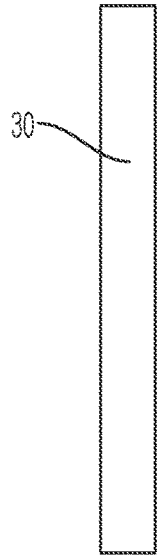
Figure 9D:
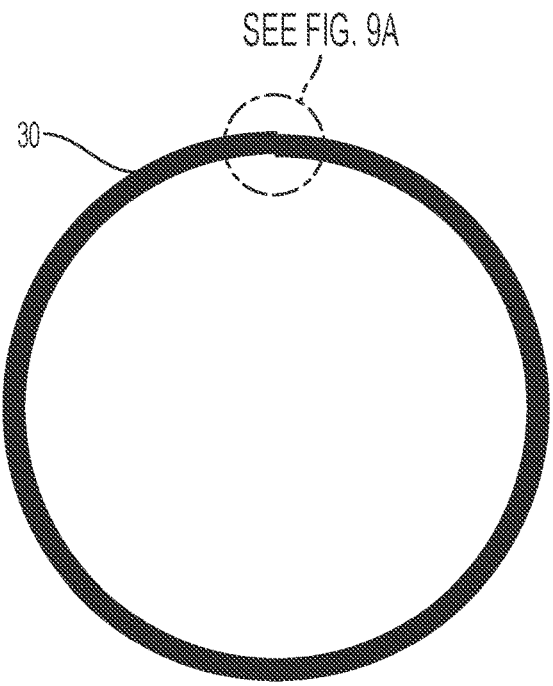
Figure 9E:
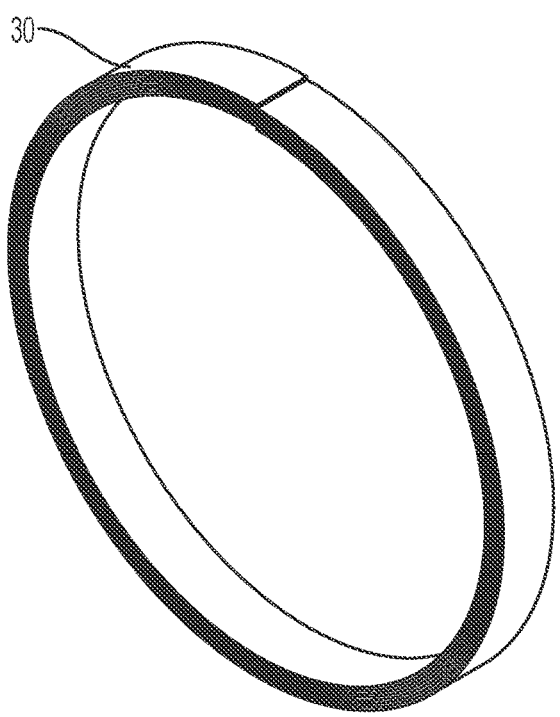
Figure 10A:
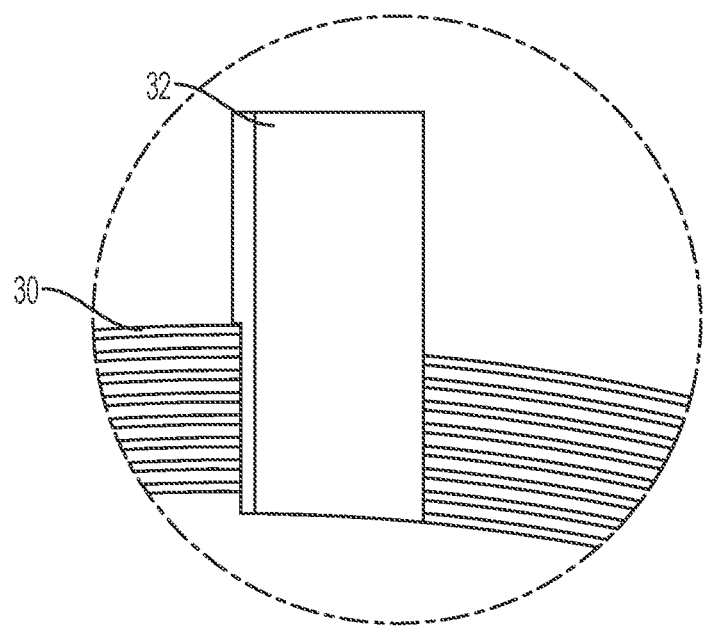
FIGS. 10A-10E depict a spiral inductive tube, according to other embodiments of the present invention.
Figure 10B:
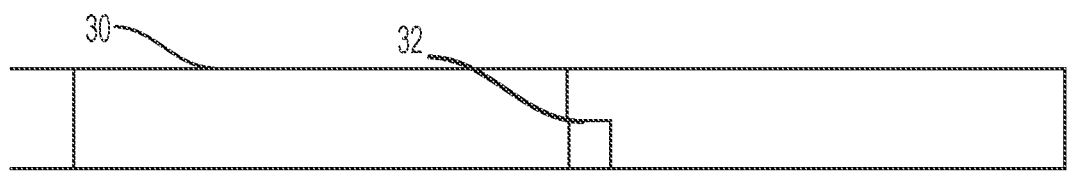
Figures 10C, 10D:
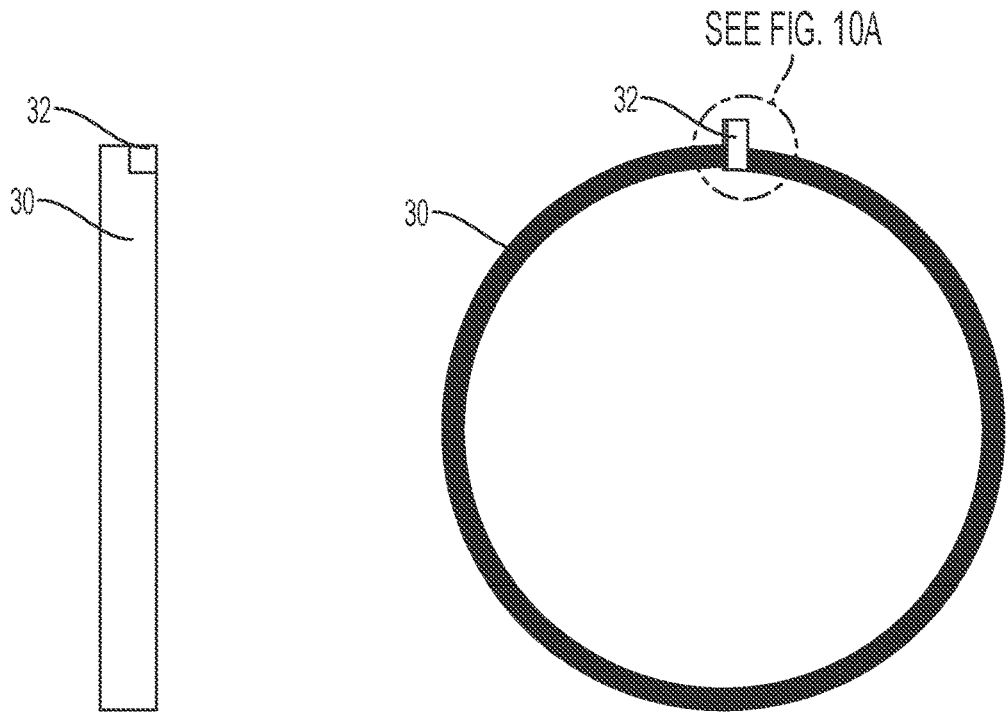
Figure 10E:
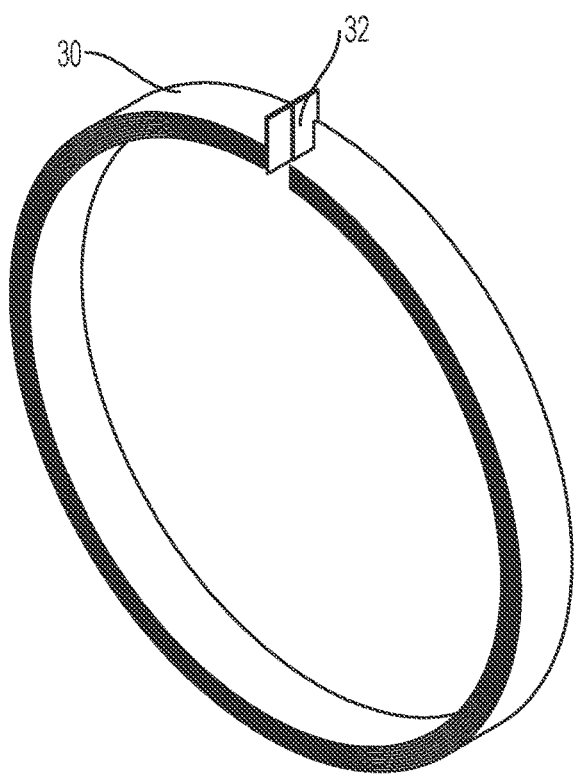

In certain embodiments, the fluid separator is connected to the peripheral area of the conduit, as shown in FIG. 8, so that the inlet nozzle and the outlet nozzle do not disturb alternating magnetic fields created by the primary inductor.

In certain embodiments, seams between the divider and the housing are sealed. In certain embodiments, seams between the plurality of elongations of the divider and the plurality of secondary inductors may be sealed. For example, in certain embodiments adhesive may be applied at seams and cured with ultraviolet light.

In certain embodiments, a fluid separator of the present disclosure is constructed of insulating materials, for example, polymers and/or plastic so that the separator does not disturb the magnetic field in any instance.

Spiral Inductive Tube

In certain embodiments, a spiral inductive tube provides a single flow path (e.g., instead of a fluid separator, a conduit, and secondary inductors) for the fluid from the inlet of the tube to the outlet. Exemplary spiral inductive tubes 30 are depicted in FIGS. 9A-9E and 10A-10E. A tube (e.g., conductive tube) may be shaped into a circular form. This is repeated multiple times using the same tube, creating the spiral inductive tube 30. The spiral tube 30 comprises one or more circular loops. The spiral tube 30 may comprise one or two extended tails (34 and 36 of FIG. 11), which can be connected to an inlet and/or outlet. The spiral tube may comprise a window 32 as shown in FIG. 10A-10E for measuring temperature of the fluid flowing.

Similar to embodiments with a plurality of thin ring-shaped secondary inductors, a primary inductor comprising a winding 55 wound on a ferrite bobbin core 56 may be inserted into a central opening of the spiral inductive tube. The primary inductor generates magnetic flux passing through the central opening, inductively coupling to the spiral inductive tube and generating local currents therein. An unheated fluid enters from one of the extended tails of the tube (e.g., fluid inlet) and flows within the spiral inductive tube, contacting the inner walls of the spiral inductive tube. Heat generated within the inductive walls of the spiral inductive tube (e.g., due to the alternating magnetic fields from the primary inductor located in the central opening of the spiral inductive tube) is transferred to the fluid flowing in the spiral inductive tube.

In certain embodiments, the spiral inductive tube comprises one or more conductive wires (e.g., copper, stainless steel) that electrically connect loops. The conductive wires further provide electrical shorts within the spiral inductive tube.

In certain embodiments, the spiral inductive tube comprises an insulating housing (e.g., polymer, plastic).

In certain embodiments, where amounts and/or properties of the fluids in the heating system vary, it may be desirable to modify certain key parameters of the spiral inductive tube. For example, it is desirable to increase or decrease inner and/or outer diameters of the spiral inductive tube, increase or decrease the number of windings, change the total surface area of the spiral inductive tube, and/or change materials used in the construction of the spiral inductive tube based on the type and/or volume of fluids to be heated. For example, in order to accommodate a higher heating capacity, the total surface area, and/or windings of the spiral inductive tube may be increased.

In certain embodiments, a spiral inductive tube is constructed of one or more conductive materials selected from the group consisting of stainless steel, carbon (graphene), silver, copper, gold, aluminum, tungsten, zinc, nickel, lithium, iron, platinum, tin, carbon steel, lead, titanium, grain oriented electrical steel, manganin, constantan, mercury, nichrome, carbon (graphite) and combinations thereof.

In certain embodiments, a spiral inductive tube has a total interior surface area of about 1 $in^2$ to about 1000 $in^2$, about 5 $in^2$ to about 1000 $in^2$, about 10 $in^2$ to about 1000 $in^2$, about 1 $in^2$ to about 500 $in^2$, about 1 $in^2$ to about 100 $in^2$, or about 1 $in^2$ to about 50 $in^2$.

In certain embodiments, an inner diameter of a spiral inductive tube ranges from about 1/32" to about 1", from about 1/16" to about 1", from about 1/32" to about 1/2", from about 1/32" to about 1/4", or from about 1/16" to about 1/4".

In certain embodiments, a spiral inductive tube winds about 1 to about 20 times, about 1 to about 10 times, or about 1 to about 5 times.

Operation

As indicated previously, the energy inductively coupled to the secondary inductors 41A-41J or the spiral inductive tube is preferably controlled to maintain a preselected temperature at the outlet of the heater. Circuitry suitable for this purpose is illustrated in FIG. 13. The temperature sensor 51 provides an output signal corresponding to the temperature at the outlet of the heater. This temperature signal is compared with a reference voltage representing a desired temperature, e.g. 42° C., by an error amplifier designated generally by reference character 63.

The error signal obtained from the error amplifier 63 is applied to a modulator 65 which modulates an amplitude cycle of a low frequency signal obtained from a sine wave oscillator 66. The pulse width of this amplitude modulated signal is in turn modulated, as indicated at 67 by a high frequency signal obtained from an oscillator 71. This results in a signal or waveform having a high frequency carrier, but with an energy content proportional to its low frequency amplitude. This signal is in turn applied through suitable driver circuitry 77 to a bridge type power output circuit 79, which provides alternating current energization of the inductor winding 55.

As will be understood by those skilled in the art, power transferred to the secondary inductors 41A-41J or the spiral inductive tube will be determined essentially by the average power content of the waveform applied to the winding 55, thus, this power will be modulated in accordance with an error signal generated by the error amplifier 63 such that the temperature at the output of a heater is maintained at a value substantially equal to the desired or set point temperature. Further, since the heat is generated in the secondary inductors 41A-41J or the spiral inductive tube themselves which are in intimate thermal contact with the fluid passing through the heater, a very high overall efficiency is obtained. Further, since the volume of fluid within the heater at any given moment is relatively small as compared with other devices, a relatively quick response is obtained and very little fluid is lost or unavailable to a patient, since the volume required to fill the system is correspondingly small.

In certain embodiments, an exemplary system of the present disclosure receives electric power by an Alternating Current (AC) wall outlet. In certain embodiments, the system is operated from battery power.

In certain embodiments, the system offers adjustability of flow rate of a fluid from 1 ml/min to 2000 ml/min, or from 10 ml/min to 2000 ml/min. As discussed herein, the system obviates clogging issues that may result from low flow of improperly treated fluids (e.g., improper or compromised anticoagulants) in dual flow path systems. Thus, the embodiments of the single flow path system described herein provide for advantageous operation at low flow rates, e.g., non-zero flow rates of less than about 100 ml/min, or less than about 50 ml/min, or less than about 40 ml/min, or less than about 30 ml/min, or less than about 20 ml/min, or less than about 15 ml/min, or less than about 10 ml/min.

In certain embodiments, an exemplary system of the present disclosure comprises a bubble trap 129 that separates air from fluid by gravitational force. For example, the bubble trap 129 may have a chamber with an inlet and an outlet. The outlet may be located at the bottom of the chamber. Any air introduced by a pump into a fluid due to gravitational force may separate from the fluid and may move to the top of the chamber, while the heated fluid (e.g., without any air bubbles) exits through the outlet from the bottom of the chamber.

A small part of the system needs to be disposable or replaceable. These parts may be replaced or disposed from use to use. All of the electronics, energizing inductor and magnetic cores can be used repeatedly. In certain embodiments, a conduit or chamber 31 is included as part of a disposable set. In certain embodiments, a plurality of secondary inductors are included as part of a disposable set. In certain embodiments, a fluid separator is included as part of a disposable set. In certain embodiments, a spiral inductive tube is included as part of a disposable set. In certain embodiments, a bubble trap is included as part of a disposable set. In certain embodiments, a housing is included as part of a disposable set. In certain embodiments, a disposable set is for a single use. A disposable set is constructed of materials that can be sterilized and made pyrogen free by conventional methods and so that single uses thereof are economically feasible.

In certain embodiments, components that the biological fluid (e.g., blood) contacts are biocompatible and/or sterilizable or replaceable.

Slack Time Heating System

Administration of cold blood and other fluids at high flow rates (e.g., greater than 500 ml/min, or greater than 750 ml/min) using an in line warming system requires the delivery of high quantities of power to the fluids. To infuse cold fluids at a rate in excess of these levels would require more energy than the typical AC outlet can supply. Certain systems store thermal energy in a separate fluid (e.g., water or oil, not infusate) for transferring the stored heat from the fluid to the infusate during times of need. Drawbacks of this approach include the necessity to later transfer energy to the infusate before/during infusion with the limited heat transfer rate of the system (e.g., due to a limited surface area between water/oil and infusate) and the potential contamination of the infusate by the fluid bath.

The present disclosure is directed to a slack-time heating system that utilizes excess heating capacity of fluid heaters to pre-warm fluid in a reservoir. The present disclosure describes a heating system to store heat energy within a reservoir (e.g., in infusate) during off peak periods (e.g., when low flow is required) for later use (e.g., when high flow is required).

Figure 12:
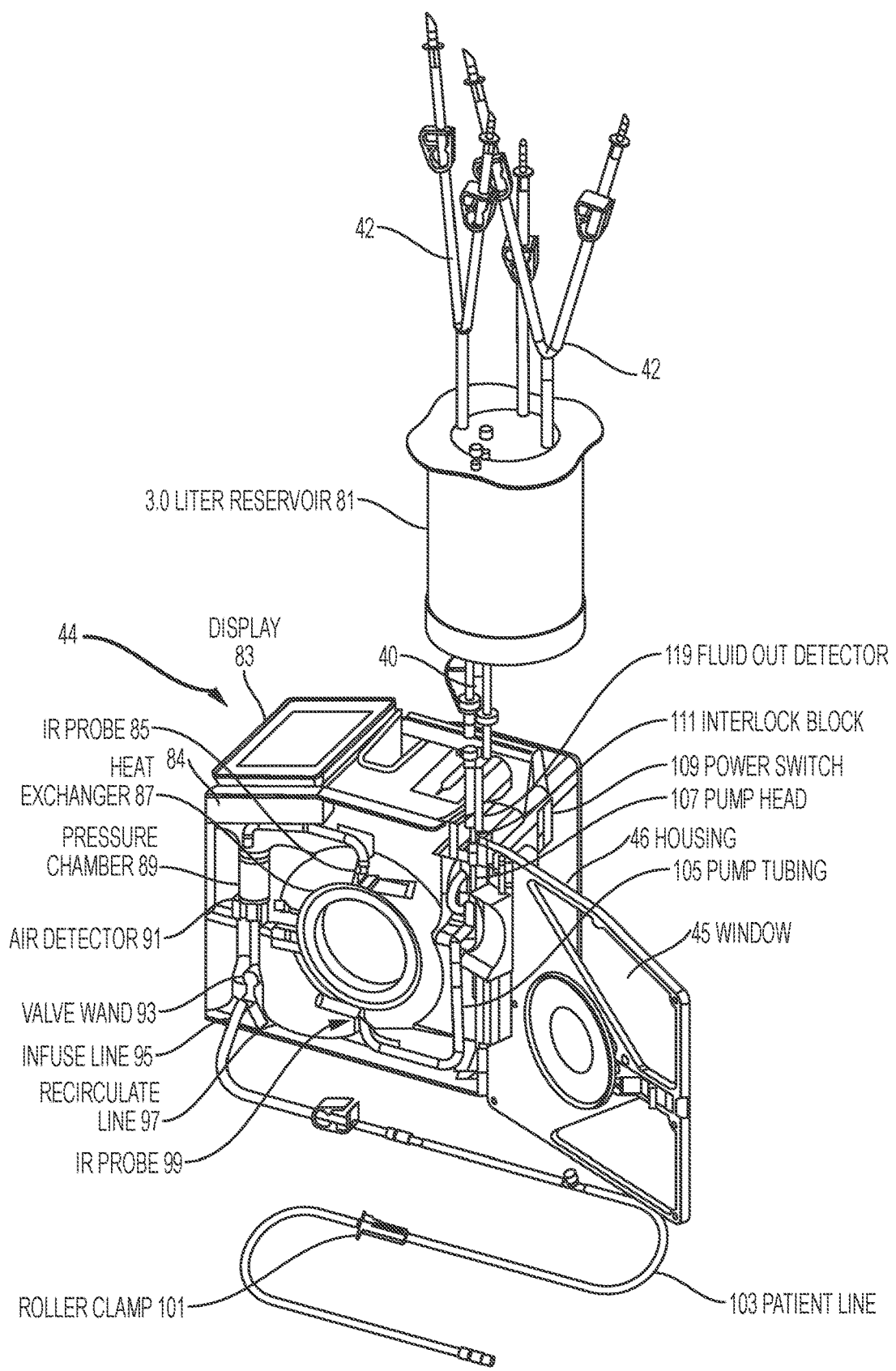
FIG. 12 is a schematic representation of a slack time heating system with an associated disposable set, according to an embodiment of the present invention.

FIG. 12 depicts an exemplary slack-time heating system. The system comprises a large volume reservoir 81 connected to a pump tubing 105 threaded through a roller pump head further connected to a heat exchanger 87. The fluid path continues to a pressure chamber 89 and then directs one path to a patient via a patient line 103 or back to the reservoir 81 via a recirculation line 97. Therapeutic infusion fluid is provided to the heating system from either one or more conventionally available IV type bags (not shown). Fluid tubular lines (not shown) and "Y" connectors 42, direct infusion fluid to reservoir 81, for storage and further use as will be described in greater detail hereinafter. Additional tubular fluid lines 40 direct the fluid from reservoir 81 to and through a therapeutic fluid processing device 44. Therapeutic fluid after being processed by device 44 is directed into a patient tubular fluid feed line 103.

Therapeutic fluid processing device 44 is of a weight, size configuration that permit it to be mounted to, and utilized when, carried by a conventional IV pole (not shown) whether, or not, such IV pole is provided with a wheel base (not shown). Device 44 may just as easily be utilized when positioned on a substantially horizontal surface such as a table, cabinet or the like as long as it is in proximity to the patient that is to undergo the intended procedure.

An air detector 91 is connected by a suitable vacuum line (not shown) to the vacuum regulator/wall suction (not shown) of the location (hospital, etc.) where patient is to be treated. Device 44 includes a housing 46 (FIGS. 2-5); which includes a top, a bottom, a left side, a right side and a back which together form a housing body and define there within a component space that houses the heating system. An access door, hingedly connected to housing body permits access into component space and to mechanisms and components housed and mounted within housing 46; as will be explained in greater detail herein after. Windows 45 formed through the access door, are covered with "Plexiglas", or similar transparent material, to facilitate observance of the processing taking place by device 44.

A conventionally available magnetic induction heater or heat exchanger 87 is securely positioned within component space of housing 46. Suitable and conventional electric power is provided to therapeutic fluid processing device 44, through a power cord (not shown) that is to be connected to an electric outlet (not shown), and there from to heat exchanger 87. A substantially conventional computer 84, also fixedly positioned within housing 46, along with its control and operating software and/or hardware, also receives power through the power cord (not shown). A touch screen display 83 connected to the computer 84 projects outside the housing 46. Device 44 may also be provided with back-up batteries (not shown) (rechargeable or otherwise) also housed within housing 46 and suitably connected to the components and mechanisms there within that require electric power to operate. A conventional roller-type peristaltic pump, also positioned within housing body 46 also receives suitable electric power through the power cord (not shown) and operates under control of computer 84 and its associated software/hardware.

Positioning grooves are formed in housing 46, to receive specific sections of tubular fluid lines. A temperature IR probe 85 is mounted proximate a fluid entry to heat exchanger 87 and another temperature probe 99 at a fluid exit from heat exchanger 87. Temperature probes 85, 99 are suitably connected to power and computer 84, and its software/hardware, and they are of the infrared type but other types of temperature probes may just as well be so mounted and used. A substantially semi-cylindrical pressure chamber well 80, formed in housing 46, uses a pressure transducer (not shown), which is also mounted in housing 46 proximate to an air detector 91. A valve wand 93 is also mounted in housing 46 between fluid line positioning grooves. A fluid out detector (not shown) is mounted proximate to fluid entry into device 44 and its fluid pump. The fluid out line can be selectively connected to the infuse line 95 that connects to the patient line 103 (e.g., to send infusate/fluid to the patient) or recirculate line 97 to send infusate/fluid to the reservoir 81 for storage.

In certain embodiments, a slack-time heating system comprises a diversion valve 93 that controls the ratio between a flow in a patient line and a flow in a recirculation line. When the diversion valve is in a recirculation position (e.g., the patient line is obstructed, while the recirculation line is opened), the pump 107 will cause fluid in a bubble trap to flow back to the reservoir (e.g., exit from the top).

In certain embodiments, the slack-time heating system described herein utilizes the heating system when it is not being actively used to infuse a patient. Then the fluid is sent from the reservoir to the heat exchanger (e.g., induction heater), is warmed, and is resent to the reservoir. Then, when the fluid (e.g., blood) is sent to the patient, pre-warmed fluid from the reservoir again passes through the heat exchanger before being sent to the patient. The amount of thermal energy that needs to be transferred to the fluid (e.g., infusate) is smaller, if the temperature difference the heat exchanger needs to achieve to heat the fluid (e.g., infusate) is lower (e.g., if the fluid going into the heat exchanger from the reservoir is pre-warmed). Thus, during a medical procedure, when the heating system is not needed, fluid can pass through the heat exchanger, and then reside in the reservoir until needed, thereby storing thermal energy. Thus, the system can heat the fluid rapidly when the infusion is needed. As the system does not use other fluids to heat the infusate, the system also does not suffer from a risk of contamination, unlike water-based heat exchangers.

In certain embodiments, reservoirs of the present disclosure mix unheated fluid and heated fluid.

In certain embodiments, the ratio of a flow in a patient line to a flow in a recirculation line is between 100:1 and 1:100.

In certain embodiments, the slack time heating system utilizes a single flow path as described in the present disclosure.

Vacuum Release Valve

Figure 14A:
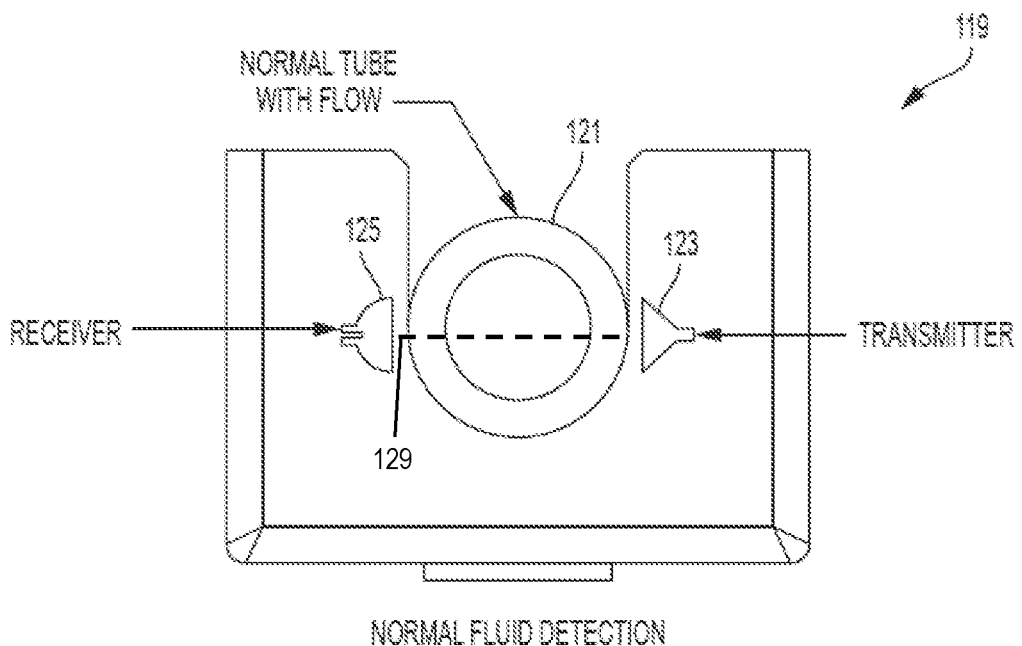
FIGS. 14A-14C demonstrate a sensor for a fluid level in a reservoir, and deformation of an inflow tubing.
Figure 14B:
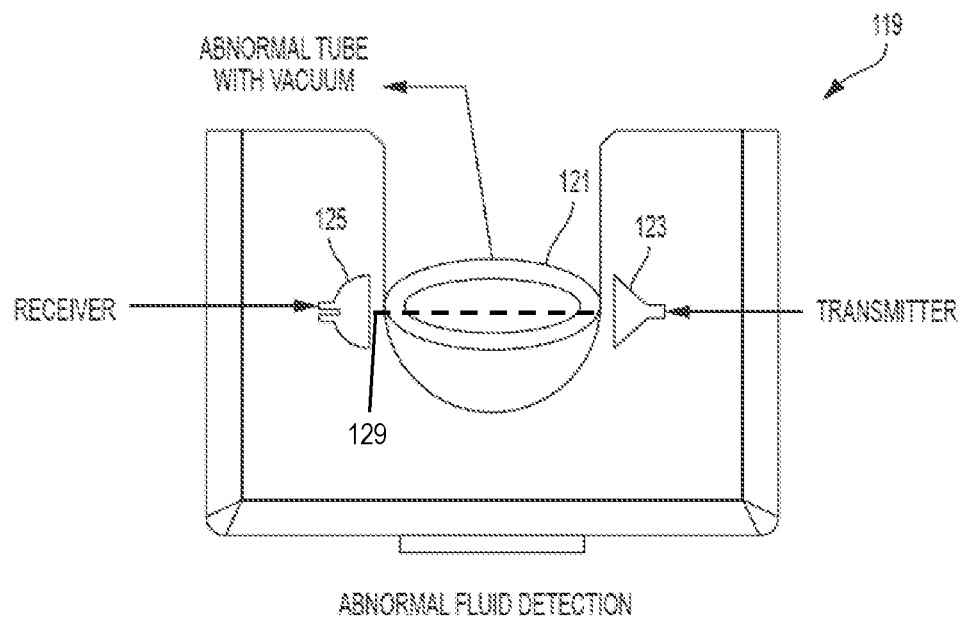
Figure 14C:
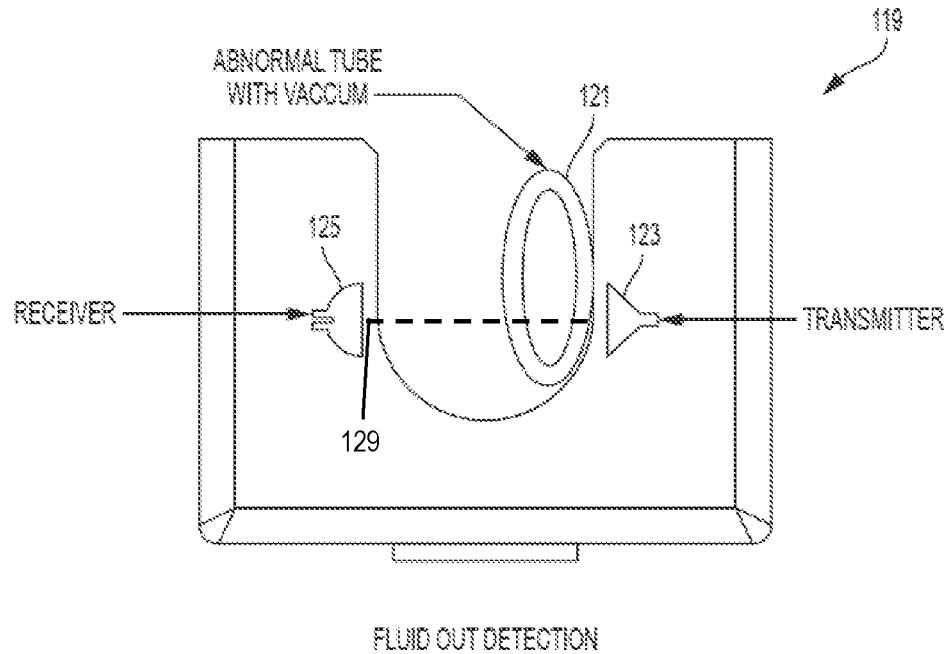

In certain embodiments, a fluid heating system has a sensor (e.g., fluid out sensor) 119 connected to an inflow tubing 121 (e.g., from an infusate reservoir to fluid heaters) to detect if an infusate reservoir is empty. Typically, the sensor comprises a transmitter 123 and a receiver 125, and measures velocity of ultrasound waves from the transmitter 123 to the receiver 125, (e.g., ultrasound travels faster through fluids than air) as shown in FIG. 14A to distinguish between a fluid-filled inflow tubing and tubing when fluid level in the infusate reservoir is low or zero. The inflow tubing 121 is located between the transmitter 123 and the receiver 125. When the fluid level in the infusate reservoir is low (or zero), the pressure in the infusate reservoir and the inflow tubing is lower than the atmospheric pressure. Therefore, the non-rigid inflow tubing 121 deforms to minimize the pressure difference. For example, the cross-section area of the inlet tubing reduces, or the cross-section of the inflow tubing becomes elliptic, as shown in FIGS. 14B and 14C. The sensor measures this deformation of the inflow tubing to detect fluid availability in the tubing and therefore, the reservoir. Since ultrasound waves travel faster through fluids than air, a fluid-filled tubing results in higher velocity ultrasound waves, than a collapsed tubing that causes air to fill any additional space between the transmitter and receiver of the sensor.

The direction of deformation affects detectability of fluid levels in the inflow tubing by the sensor. The pressure difference between the inside of the non-rigid inflow tubing and the outside atmospheric pressure may result in the tubing collapsing from a circular cross-section into an elliptical cross-section. For example, a major axis of the elliptic cross-section of the collapsed inflow tubing can be perpendicular to a line between the transmitter and the receiver as shown in FIG. 14C, or parallel to that line as shown in FIG. 14B. If the major axis of the elliptic cross-section of the collapsed inflow tubing is not parallel (e.g., perpendicular) to the line between the transmitter and the receiver, the sensor can measure the deformation properly as the ultrasound now travels in air more than before the deformation of the inflow tubing occurred. However, if the major axis of the elliptic cross-section of the collapsed inflow tubing is parallel to a line between the transmitter and the receiver, the sensor cannot detect the deformation because of lack of air in the ultrasound beam path 129.

The present disclosure is directed to a fluid heating system that includes a vacuum release valve to prevent the undesired orientation of the deformed inflow tubing. In certain embodiments, the vacuum release valve supplies air to the tubing to reduce pressure difference between the inflow tubing and the surroundings, preventing the deformation of the inflow tubing.

Figure 15A:
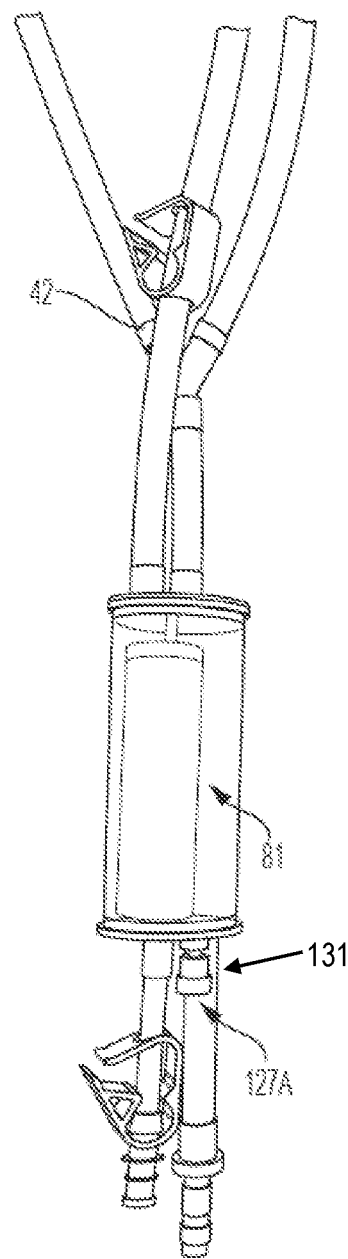
FIGS. 15A-15C depict exemplary disposable set with vacuum release valve, according to an embodiment of the present invention.
Figure 15B:
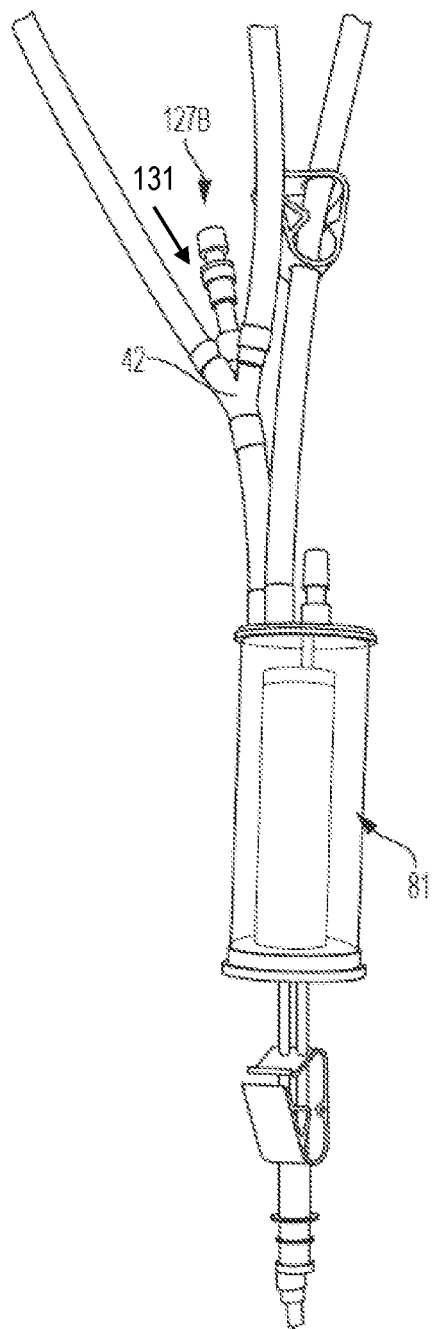
Figure 15C:
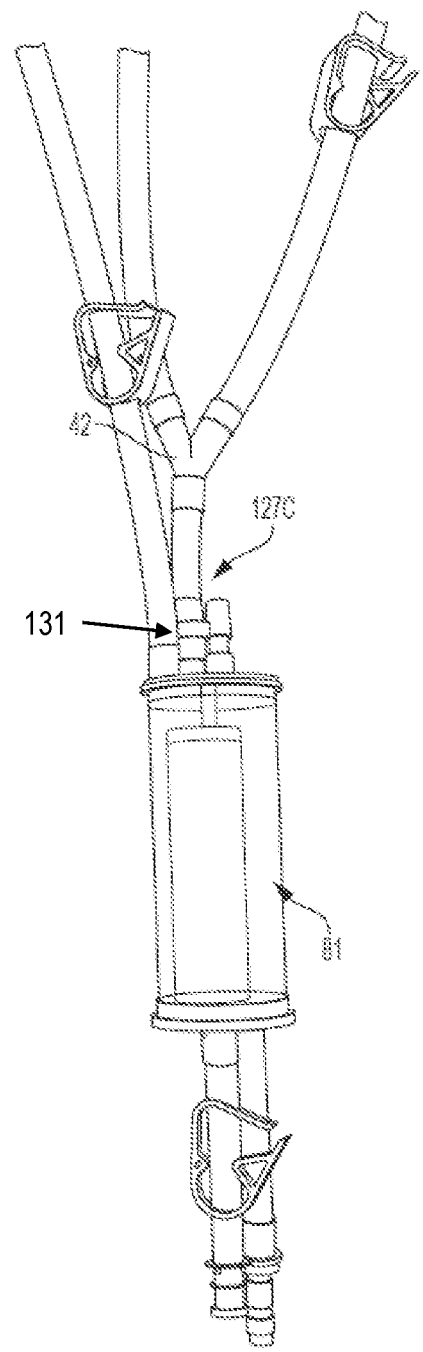
Figure 16:
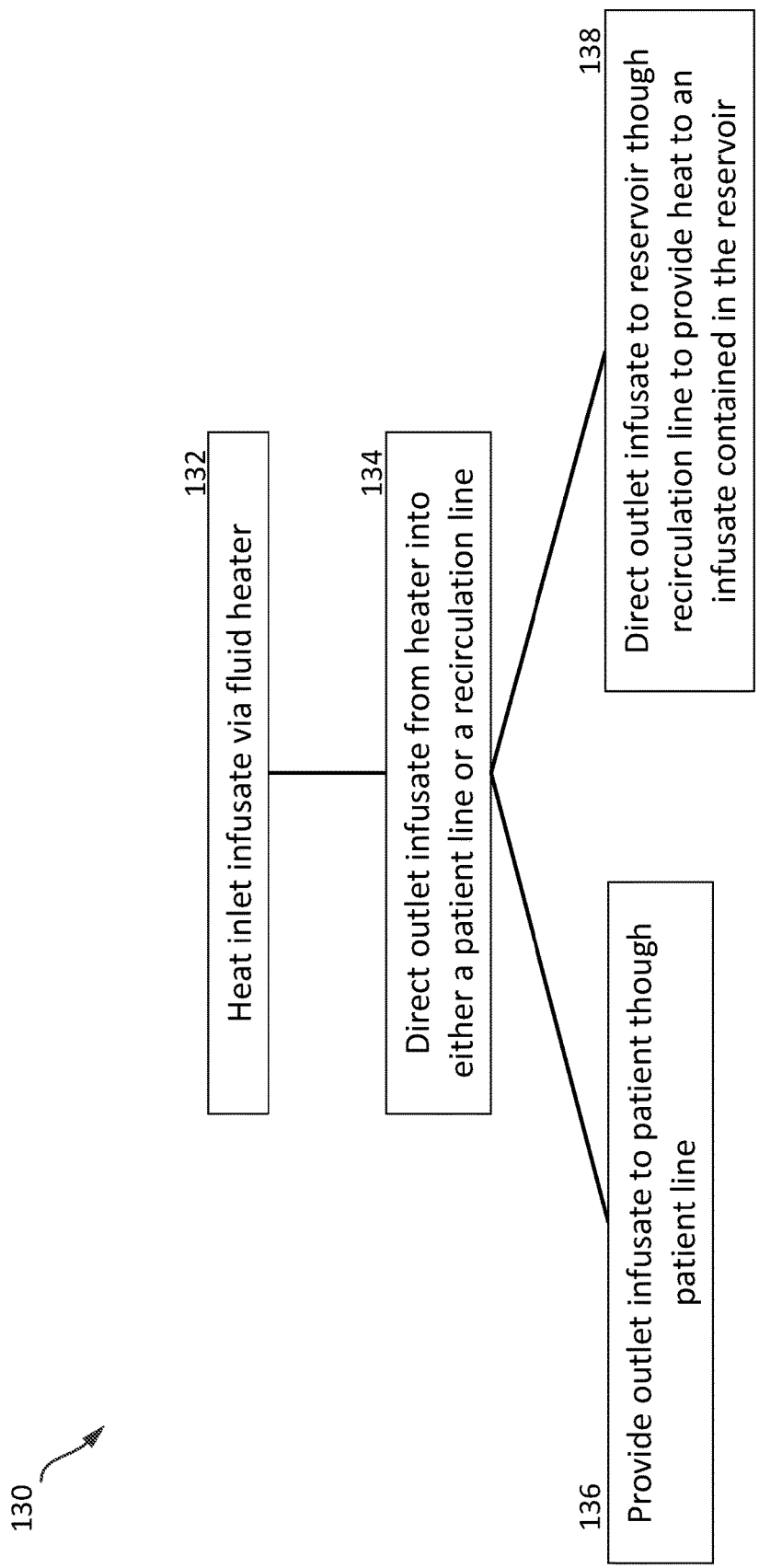
FIG. 16 depicts a method for heating an infusate, according to an embodiment of the present invention.

FIGS. 15A-15C depict exemplary disposable sets with vacuum release valves. In certain embodiments, the vacuum release valve 127A is connected on the bottom of the reservoir (FIG. 15A). The inflow tubing and the vacuum release valve may be parallel to each other. In certain embodiments, the vacuum release valve 127C is connected on the top of the reservoir (FIG. 15C). In certain embodiments, the vacuum release valve is indirectly connected to the reservoir. The reservoir may comprise a tubing attached to the top of the reservoir (FIG. 15B). The vacuum release valve 127B may be connected to the reservoir through the tubing.

Any type of suitable vacuum release valve may be used in accordance with the disclosure. In certain embodiments, the vacuum release valve may comprise a housing and a regulator. In certain embodiments, the vacuum release valve may operate automatically (e.g., without an operator). The vacuum release valve is normally closed (e.g., the vacuum release valve does not allow air into the inflow tubing, e.g., the regulator presses against a portion of the housing, thereby blocking air passage). When the pressure difference between the system (e.g., the reservoir, inflow tubing) and the atmosphere reaches a pre-determined value (e.g., 0.5, 1, 2, 3, 4, 5, 6, 7, 8, 9, or 10 psi), the vacuum release valve opens (e.g., the valve allows air to flow into the system). The pre-determined value may be manipulated by varying an external force applied to the regulator. For example, if the pressure difference between the system (e.g., the reservoir, inflow tubing) and the atmosphere exceeds the applied force per area, the valve opens. The force may be applied mechanically (e.g., spring, diaphragm) to the regulator.

In certain embodiments, the vacuum release valve supplies air to the disposable set when the pressure of the disposable set is 0.5, 1, 2, 3, 4, 5, 6, 7, 8, 9, or 10 psi lower than atmospheric pressure.

In certain embodiments, the vacuum release valve comprises a filter 131, and/or a sanitation unit to provide sterile air to the system.

In certain embodiments, a vacuum release valve is included as part of a disposable set.

EXEMPLIFICATION

Single Flow Path

The present example describes, among other things, an exemplary operation of single flow path induction heater with an exemplary spiral inductive tube.

Figure 11:
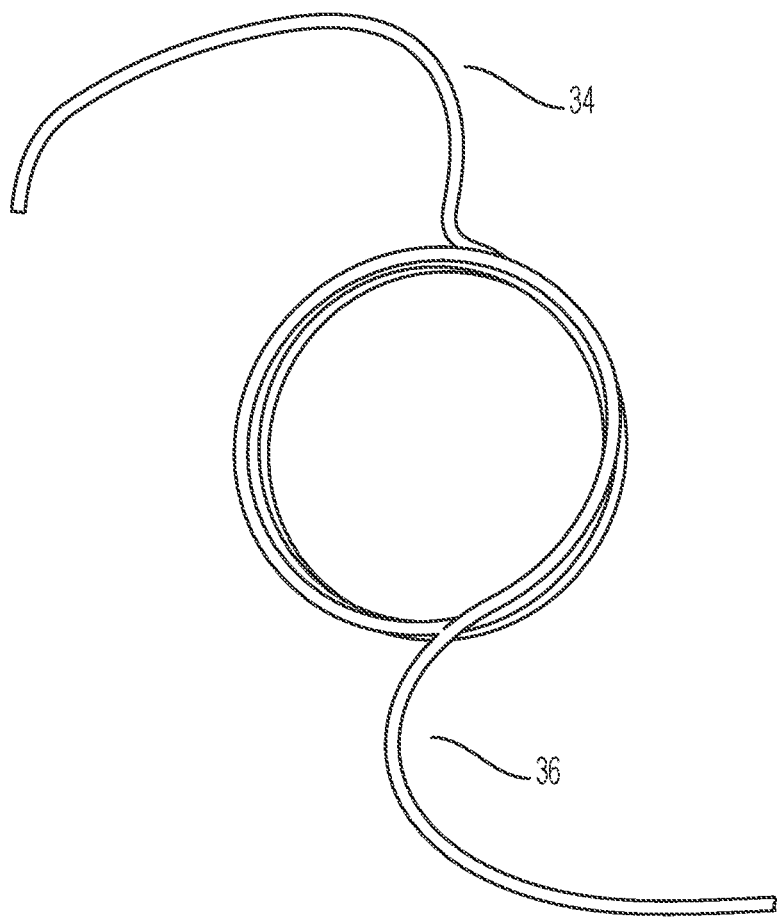
FIG. 11 shows a spiral inductive tube, according to an embodiment of the present invention.

As shown in FIG. 11, aluminum tubing with an inner diameter of ⅛" and an outer diameter of 3/16" was shaped into a circular form to be operated within the Belmont® Rapid Infuser by Belmont. Circular loops with 2.5 overlapping turns and extended tails were created. Copper wire was wrapped around the input and output in order to provide electrical connection with in the tubing. The tails are positioned in a fashion so that the input and output thermal detectors are as close as possible to the input and the output. The spiral inductive tube was successfully installed in the Belmont® Rapid Infuser. The system pumped fluid through the tubing. Temperature of the outlet fluid was increased relative to temperature of the inlet fluid.

Vacuum Release Valve

The present example describes, among other things, exemplary operations of a rapid heating system with exemplary vacuum release valves.

Disposable sets (e.g., The Belmont® 3-Spike Disposable Set) with various vacuum release valves as shown in FIGS. 15A-15C were tested with the Belmont Rapid Infuser. A vacuum release valve was connected to the 4.4 L reservoir (FIG. 15A), a y-connection at the intersection of tubing (FIG. 15B), or onto the filter assembly (FIG. 15C). The modified disposable sets and an unmodified set were then tested. Testing mediums were water, sodium chloride and water at 35.7 grams per 100 mL, and a 50/50 mix of water and glycerin by volume. Each modified disposable set was tested at a wide range of flow rates. While the unmodified set was clamped off due to deformation of the inflow tubing as pressure decreased, the vacuum release valve of the modified sets allowed air to be drawn into the set, and did not experience clamping off. Once the reservoir was sufficiently emptied, air would be drawn into the fluid path causing the fluid out detector to register the low levels of fluid in the heating system and to turn off the machine properly. The valve worked successfully with all testing mediums and at any flow rate. The addition of the vacuum release valve prevented the improper deformation of tubing.

What is claimed is:

1. A disposable unit of a system for heating a fluid, the disposable unit comprising:
   a conduit, defining a central opening;
   one or more secondary inductors within the conduit;
   an inflow tubing connected to the conduit;
   a reservoir for containing an infusate fluid;
   a vacuum release valve connected to the reservoir; and
   a sensor comprising a transmitter and a receiver, the sensor configured to measure a velocity of ultrasound waves from the transmitter to the receiver, the inflow tubing being disposed between the transmitter and the receiver, the sensor configured to detect a presence of air in the inflow tubing along an ultrasound beam path,
   wherein each of the one or more secondary inductors is substantially parallel, and
   wherein, when pressure in the inflow tubing is lower than atmospheric pressure, the vacuum release valve allows flow of air into the inflow tubing in order to reduce a pressure difference between the inflow tubing and the atmospheric pressure, thereby preventing and/or reducing deformation of the inflow tubing, and detecting a fluid out condition.

2. The disposable unit of claim 1,
   wherein the vacuum release valve prevents undesired orientation of the inflow tubing.

3. The disposable unit of claim 2,
   wherein the vacuum release valve supplies air to the inflow tubing when the pressure within the inflow tubing is 5 psi lower than the atmospheric pressure.

4. The disposable unit of claim 3, wherein the vacuum release valve is connected to the top of the reservoir.

5. The disposable unit of claim 1, wherein the reservoir further comprises a tubing attached to the top of the reservoir, and the vacuum release valve is connected to the reservoir through the tubing, and
   wherein the vacuum release valve comprises an air filter.

6. The disposable unit of claim 1, further comprising a fluid separator comprising an inlet nozzle and an outlet nozzle.

7. The disposable unit of claim 6, wherein the bubble trap separates air from the fluid by gravitational force.

8. The disposable unit of claim 5, further comprising a bubble trap for removing air bubbles from fluid flowing through the system.

9. The disposable unit of claim 6, wherein the inlet nozzle directs unheated fluid to the conduit,
   wherein the outlet nozzle receives heated fluid from the conduit, and
   wherein the inlet nozzle and the outlet nozzle are parallel to each other to allow flow through the outlet nozzle in an opposite direction to flow through the inlet nozzle.

10. The disposable unit of claim 6, wherein the fluid separator comprises a housing comprising:
    an inlet chamber;
    an outlet chamber adjacent the inlet chamber; and
    a divider separating the inlet chamber and outlet chamber.

11. The disposable unit of claim 6, wherein each of the inlet nozzle and the outlet nozzle comprises a semi-circular cross-section, and
    wherein the semi-circular cross-section of the inlet nozzle is oriented such that the semi-circular cross-section of the inlet nozzle is a mirror image of the semi-circular cross-section of the outlet nozzle along a length of the fluid separator.

12. The disposable unit of claim 11, further comprising a divider separating the inlet chamber and outlet chamber,
    wherein the divider is removable, and
    wherein the semi-circular cross-sections of the inlet and the outlet are located on opposite sides of the fluid divider so that the divider can separate the inlet and the outlet when the divider is positioned therebetween.

13. The disposable unit of claim 1, comprising a primary inductor comprising:
    a ferrite bobbin core; and
    a winding wound around the ferrite bobbin core;
    wherein the primary inductor generates a magnetic flux that passes through the central opening; and
    wherein the primary inductor is inductively coupled to a plurality of secondary inductors disposed concentrically about the primary inductor,
    the disposable unit further comprising two ferrite magnetic end plates, wherein the primary inductor and the plurality of secondary inductors are disposed between the two ferrite magnetic end plates, and
    wherein the two ferrite magnetic end plates improve the degree of coupling between the winding and the secondary inductors.

14. The disposable unit of claim 13, wherein the fluid separator comprises a housing comprising:
    an inlet chamber;
    an outlet chamber adjacent the inlet chamber; and
    a divider separating the inlet chamber and outlet chamber, the divider comprising:
      a solid upper portion to separate the inlet chamber and the outlet chamber when the divider is secured in the fluid separator; and
      a lower portion comprising a plurality of elongations to accommodate the plurality of secondary inductors,
    wherein each elongation of the plurality of elongations occupies completely and blocks a gap between any two successive secondary inductors of the plurality of secondary inductors, thereby causing the plurality of elongations to prevent mixing of unheated fluid and heated fluid flowing between the secondary inductors, and
    wherein each of the plurality of elongations comprises a thickness substantially identical to each gap between the secondary inductors.

15. A system comprising the disposable unit of claim 1, the system further comprising:
- a housing for containing at least a portion of the disposable unit;
- a plurality of fluid line positioning grooves formed in the housing for receiving one or more sections of tubular fluid lines, the tubular fluid lines being in fluid communication with the inflow tubing; and
- a valve wand mounted in the housing between the plurality of fluid line positioning grooves.

16. The system of claim 15, wherein the one or more sections of tubular fluid lines comprise a patient line and a recirculation line.

17. The system of claim 16, wherein the valve wand controls a flow ratio between the patient line and the recirculation line.

18. The system of claim 15, configured to operate with an infusate flow rate in a range from 1 ml/min to 2000 ml/min.

19. The system of claim 18, configured to operate with a sustained infusate flow rate under 50 ml/min.

20. A disposable unit of a system for heating a fluid, the disposable unit comprising:
- a conduit, defining a central opening;
- one or more secondary inductors within the conduit;
- an inflow tubing connected to the conduit;
- a vacuum release valve; and
- a sensor for measuring any deformation in the inflow tubing in order to detect fluid availability in the inflow tubing, the fluid out sensor comprising a transmitter and a receiver, the inflow tubing being disposed between the transmitter and the receiver, the fluid out sensor configured to measure a velocity of ultrasound waves from the transmitter to the receiver and thereby detect a presence of air in the inflow tubing along an ultrasound beam path when a change in the velocity occurs,
- wherein, when pressure in the inflow tubing is lower than atmospheric pressure, the vacuum release valve allows flow of air into the inflow tubing in order to reduce a pressure difference between the inflow tubing and the atmospheric pressure, thereby preventing and/or reducing deformation of the inflow tubing, and
- wherein, when deformation of the inflow tubing occurs, the vacuum release valve prevents an unavailability of fluid in the inflow tubing from being undetected by the fluid out sensor as a result of the flow of air into the inflow tubing.

* * * * *